United States Patent
Knudson et al.

(10) Patent No.: US 6,701,932 B2
(45) Date of Patent: *Mar. 9, 2004

(54) METHOD AND APPARATUS FOR REVASCULARIZING A CORONARY VESSEL WITH AN IMPLANT HAVING A TAPERED MYOCARDIAL LEG

(75) Inventors: Mark B. Knudson, Shoreview, MN (US); William L. Giese, Arlington, VA (US)

(73) Assignee: Percardia, Inc., Merrimack, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/043,684

(22) Filed: Jan. 9, 2002

(65) Prior Publication Data

US 2002/0065478 A1 May 30, 2002

Related U.S. Application Data

(63) Continuation of application No. 09/326,819, filed on Jun. 7, 1999, now Pat. No. 6,454,794, which is a division of application No. 08/882,397, filed on Jun. 25, 1997, now Pat. No. 5,944,019, which is a continuation-in-part of application No. 08/689,773, filed on Aug. 13, 1996, now Pat. No. 5,755,682.

(51) Int. Cl.⁷ ............................................. A61B 17/00
(52) U.S. Cl. ................................................... 128/898
(58) Field of Search ........................ 128/898; 606/153, 606/154, 155, 156, 159, 192, 194, 195, 198; 600/16, 17, 18; 623/11.11, 23.64, 23.68, 1.13, 1.24, 1.3, 1.31, 1.32, 1.49, 2.1, 1.1

(56) References Cited

U.S. PATENT DOCUMENTS

| | | |
|---|---|---|
| 2,127,903 A | 8/1938 | Bowen |
| 3,042,021 A | 7/1962 | Read |
| 3,995,617 A | 12/1976 | Watkins et al. |

(List continued on next page.)

FOREIGN PATENT DOCUMENTS

| | | |
|---|---|---|
| EP | 0 515 867 A1 | 12/1992 |
| RU | 2026640 C1 | 1/1995 |
| SU | 1754128 A1 | 8/1992 |
| WO | WO 93/00868 | 1/1993 |
| WO | WO 95/35065 | 12/1995 |
| WO | WO 96/00033 | 1/1996 |
| WO | WO 96/04854 | 2/1996 |
| WO | WO 96/05773 | 2/1996 |
| WO | WO 97/13463 | 4/1997 |
| WO | WO 97/13471 | 4/1997 |
| WO | WO 97/27893 | 8/1997 |
| WO | WO 97/27897 | 8/1997 |
| WO | WO 97/27898 | 8/1997 |
| WO | WO 98/08456 | 3/1998 |
| WO | WO 98/46115 | 10/1998 |

OTHER PUBLICATIONS

U.S. Patent application Ser. No. 60/005,164, Makower.
U.S. Patent application Ser. No. 60/010,614, Makower.
"Expandable Intraheptic Protacaval Shunt Stents" Julio Palmaz et al., AJR:145, pp. 821–825, Oct. 1985.
"Expandable Intraheptic Protacaval Shunt" Julio Palmaz et al., AJF:147, pp. 1251–1254, Dec. 1986.

(List continued on next page.)

*Primary Examiner*—David J. Isabella
(74) *Attorney, Agent, or Firm*—Finnegan, Henderson, Farabow, Garrett & Dunner LLP

(57) ABSTRACT

A method for revascularizing a coronary vessel with a conduit through the heart wall having a diameter transition in the myocardial leg, wherein blood flow is in the direction of transition from larger to smaller diameter. A method for revascularizing a coronary vessel using an implant with a myocardial leg having a maximum cross-sectional area proximate a first end, and inserting the first end through the myocardium into a heart chamber so that the implant directs blood flow into the coronary vessel. A transmyocardial implant with a myocardial leg including point of minimum diameter and a first end with a larger diameter, and a vessel leg in fluid communication with the myocardial leg.

5 Claims, 20 Drawing Sheets

U.S. PATENT DOCUMENTS

| | | | |
|---|---|---|---|
| 4,086,665 A | | 5/1978 | Poirier |
| 4,118,806 A | | 10/1978 | Porier |
| 4,441,215 A | * | 4/1984 | Kaster .................... 623/1.53 |
| 4,546,499 A | | 10/1985 | Possis et al. |
| 4,562,597 A | | 1/1986 | Possis et al. |
| 4,581,017 A | | 4/1986 | Sahota |
| 4,601,718 A | * | 7/1986 | Possis et al. ............ 623/1.26 |
| 4,712,551 A | | 12/1987 | Rayhanabad |
| 4,769,031 A | | 9/1988 | McGough et al. |
| 4,788,975 A | | 12/1988 | Shturman et al. |
| 4,861,330 A | | 8/1989 | Voss |
| 4,862,886 A | | 9/1989 | Clarke et al. |
| 4,902,289 A | | 2/1990 | Yannas |
| 4,953,553 A | | 9/1990 | Tremulis |
| 4,955,856 A | | 9/1990 | Phillips |
| 4,985,014 A | | 1/1991 | Orejola |
| 4,995,857 A | | 2/1991 | Arnold |
| 5,054,484 A | | 10/1991 | Hebeler, Jr. |
| 5,071,406 A | | 12/1991 | Jang |
| 5,143,093 A | | 9/1992 | Sahota |
| 5,190,058 A | | 3/1993 | Jones et al. |
| 5,209,731 A | | 5/1993 | Sterman et al. |
| 5,254,097 A | | 10/1993 | Schock et al. |
| 5,256,150 A | | 10/1993 | Quiachon et al. |
| 5,275,622 A | | 1/1994 | Lazarus et al. |
| 5,287,861 A | | 2/1994 | Wilk |
| 5,370,685 A | | 12/1994 | Stevens |
| 5,383,925 A | | 1/1995 | Schmitt |
| 5,395,349 A | | 3/1995 | Quiachon et al. |
| 5,409,019 A | | 4/1995 | Wilk |
| 5,425,705 A | | 6/1995 | Evard et al. |
| 5,429,144 A | | 7/1995 | Wilk |
| 5,443,497 A | | 8/1995 | Venbrux |
| 5,452,733 A | | 9/1995 | Sterman et al. |
| 5,458,574 A | | 10/1995 | Machold et al. |
| 5,484,418 A | | 1/1996 | Quiachon et al. |
| 5,489,295 A | | 2/1996 | Piplani et al. |
| 5,501,698 A | | 3/1996 | Roth et al. |
| 5,505,725 A | | 4/1996 | Samson et al. |
| 5,655,548 A | | 8/1997 | Nelson et al. |
| 5,662,124 A | | 9/1997 | Wilk |
| 5,676,696 A | | 10/1997 | Marcade |
| 5,755,682 A | * | 5/1998 | Knudson et al. ............... 604/8 |
| 5,830,222 A | | 11/1998 | Makower |
| 5,944,019 A | * | 8/1999 | Knudson et al. ........... 128/898 |
| 6,350,248 B1 | | 2/2002 | Knudson et al. |
| 6,361,519 B1 | | 3/2002 | Knudson et al. |

OTHER PUBLICATIONS

"Percutaneous Transjugular Portosystemic Stent", Gerald Zemel et al., JAMA, vol. 266, No. 3, Jul. 17, 1991, pp. 390–393.

"Transjugular Intraheptic Portocaval Stent" Goetz M. Richter et al., Hepatic and Billard Radiology, pp. 1027–1030, vol. 174, Mar. 1990.

Alfred Goldman, M.D., et al., *Experimental Methods for Producing a Collateral Circulation to the Heart Directly from the Left Ventricle*, 31 J. Thoracic Surg. 364–374 (Mar. 1956).

Andrews et al., *Assessment of Feasibility for Endovascular Prosthetic Tube Correction of Aortic Aneurysm*, 82 Brit. J. of Surgery 917–919 (1995).

Banning G. Lary, MD, et al., *Myocardial Revascularization Experiments Using the Epicardium* Achives of Surgery, vol. 98, No. 1, pp. 69–72 (Jan. 1969).

Black, Martin M. et al., *Design and FlowCharacteristics*, p. 4, *Replacement Cardiac Valves*, Bodner, Endre et al., Editors, Pergamon Press (1991) (title page, p. v and p. 4 reproduced).

Bojan Cercek, M.D. et al., *Growth Factors in Pathogenesis of Coronary Arterial Restenosis*, 68 Am. J. Cardiology 24C–33C (Nov. 4, 1991).

Bruce F. Waller & Cass A. Pinkerton, *The Pathology of Interventional Coronary Artery Techniques and Devices*, in 1 Topol's Textbook of Interventional Cardiology 449–476 (Eric J. Topol ed., 2nd ed. 1994).

Carmelo A. Milano, M.D. et al., *Mediastinitis After Coronary Artery Bypass Graft Surgery*, 92 Circulation 2245–2251 (Oct. 15, 1995).

Combined Search and Examination Report Under Sections 17 & 18(3) dated Nov. 10, 1997 on UK Patent Application No. GB 9717116.9.

Currently pending claims in U.S. patent application Ser. No. 08/689,773, filed Aug. 13, 1996.

Daniel S. Schwartz, M.D. et al., *Minimally Invasive Cardiopulmonary Bypass with Cardioplegic Arrest: A Closed Chest Technique with Equivalent Myocardial Protection*, 111 J. Thoracic & Cardiovascular Surgery 556–566 (Mar. 1996).

Enio Buffolo, M.D. et al., *Coronary Artery Bypass Grafting Without Cardiopulmonary Bypass*, 61 Annals of Thoracic Surgery 63–66 (1996).

Frank M. Galioto, Jr., M.D., et al., *Right Coronary Artery to Left Ventricle Fistula*, 82 American Heart Journal 93–97 (Jul. 1971).

Fumihiko Kajiya et al., *Endocardial Coronary Microcirculation of the Beating Heart*, in Interactive Phenomena in the Cardiac System, 173–180 (S. Sideman and R. Beyar eds. 1993).

Fumihiko Kajiya et al., *Velocity Profiles and Phasic Flow Patterns in the Non–Stenotic Human Left Anterior Descending Coronary Artery During Cardiac Surgery*, 27 Cardiovascular Res. 845–850 (1993).

Fumihiko Kajiya, M.D., Ph.D. et al., *Mechanical Control of Coronary Artery Inflow and Vein Outflow*, 53 Japanese Circulation J. 431–439 (May 1989).

George Silvay, M.D., Ph.D. et al., *Cardiopulmonary Bypass for Adult Patients: A Survery of Equipment and Techniques*, 9 J. of Cardiothoracic & Vascular Anesthesia 420–424 (Aug. 1995).

Gerald D. Buckberg, MD, *Update on Current Techniques on Myocardial Protection*, 60 Annals of Thoracic Surgery, 805–814 (1995).

Hausdorf et al., *Radiofrequency–Assisted "Reconstruction" of the Right Ventricular Outflow Tract in Muscular Pulmonary Atresia with Ventricular Septal Defect*, 69 Br Heart J. 343–346 (1993).

Ian Munro, et al., *The Possibility of Myocardial Revascularization by Creation of a Left Ventriculocoronary Artery Fistula*, 58 J. Thoracic & Cardiovascular Surgery 25–32 (Jul. 1969).

International Search Report dated Dec. 11, 1997 on PCT/US9713980.

Jerome Segal, M.D. et al., *Alterations of Phasic Coronary Artery Flow Velocity in Humans During Percutaneous Coronary Angioplasty* 20 J. Am. College of Cardiology 276–280 (Aug. 1992).

John Stevens, M.D. et al., *Port–Access Coronary Artery Bypass Grafting: A Proposed Surgical Method*,111 J. Thoracic & Cardiovascular Surgery (Mar. 1996).

Kit V. Arom, M.D., Ph.D. et al., *Patient Characteristics, Safety, and Benefits of Same–Day Admission for Coronary Artery Bypass Grafting*, 61 Annals of Thoracic Surgery 1136–1140 (1996).

Kohmoto, et al., *Does Blood Flow Through Holmium: YAG Transmyocardial Laser Channels?*, 61 Ann. Thorac. Surg. 861–868 (1996).

L. Levinsky, et al., *The Revival of the Horseshoe Graft*, The Thoracic and Cardiovascular Surgeon, vol. 27, No. 5 (Oct. 1979).

Ladislav Kuzela et al., *Experimental Evaluation of Direct Transventricular Revascularization* Journal of Thoracic and Cardiovascular Surgery, vol. 57, No. 6, pp. 770–773 (Jun. 1969).

Larry R. Kaiser et al., *Video–Assisted Thoracic Surgery: The Current State of the Art*, 165Am. J. Roentgenology 1111–1117 (Nov. 1995).

Louagie et al., *Operative Risk Assessment in Coronary Artery Bypass Surgery, 1990–1993: Evaluation of Perioperative Variables*, 43 Thoracic Cardiovascular Surgeon 134–141 (1995).

Ludwig K. Von Segesser, Arterial Grafting for Myocardial Revascularization: Indications, Surgical Techniques and Results 4–5, 38–39, 48–80 (1990).

Mahmood Mirhoseini, M.D., et al.,*New Concepts in Revascularization of the Myocardium*, 45 Annals of Thoracic Surgery 415–420 (Apr. 1988).

Mark Vienna, M.D., *Minimally Invasive Surgery*, 46 Ann. Rev. Med. 147–158 (1995).

Mark W. Connolly & Robert A. Guyton, *Cardiopulmonary Bypass and Intraoperative Protection*, in Hurst's The Heart 2443–450 (Robert C. Schlant & R. Wayne Alexander eds., 8th ed. 1994).

Martin Schneider, M.D. et al., *Transcatheter Radiofrequency Perforation and Stent Implantations for Palliation of Pulmonary Artesia in a 3060–g Infant*, 34 Catheterization and Cardiovascular Diagnosis 42–45 (1995).

Massimo, M.D., et al., *Myocardial Revascularization by a New Method of Carrying Blood Directly From the Left Ventricular Cavity into the Coronary Circulation*, 34 J. Thoracic Surg. 257–264 (Aug. 1957).

Michael D. Dake, M.D. et al., *Transluminal Placement of Endovascular Stent–Grafts for the Treatment of Descending Thoracic Aortic Aneurysms*, 331 N.E.J.M. 1729–1734 (Dec. 29, 1994).

Michael L. Marin, M.D. et al., *Initial Experience with Transluminally Placed Endovascular Grafts for the Treatment of Complex Vascular Lesions*, 222 Annals of Surgery 449–469 (Oct. 1995).

Minoru Hongo, M.D. et al., *Effects of Heart Rate on Phasic Coronary Blood Flow Pattern and Flow Reserve in Patients with Normal Coronary Arteries: A Study with an intravascular Doppler Catheter and Spectral Analysis*, 127 Am. Heart J. 545–551 (Mar. 1994).

Mirhoseini, M.D., et al., *Myocardial Revascularization by Laser: A Clinical Report*, 3 Lasers in Surgery and Medicine 241–245 (1983).

Nishida, *Flow Study of Surgical Coronary Artery Fistula as an Alternative to Sequential Bypass*, 3 Cardiovascular Surgery 375–380 (Aug. 1995).

Nollert et al., *Use of the Internal Mammary Artery as a Graft in Emergency Coronary Artery Bypass Grafting after Failed PTCA*, 43 Thoracic Cardiovascular Surgeon 142–147 (1995).

Noritake Houki et al.,*A Simulation of Coronary System—A Theoretical Analysis of Intramyocardial Flow Distribution Mechanism*, 41 Japanese Circulation J. (Nov. 1977).

Peter Whittaker, Ph.D. et al., *Transmural Channels Can Protect Ischemic Tissue*, 93 Circulation 143–IS2 (Jan. 1, 1996).

Prospectus of CardioGenesis Corporation, May 21, 1996, pp. 1–59.

Prospectus of CardioThoracic Systems, Apr. 18, 1996, pp. 1–61, F1–F20.

Prospectus of CardioThoracic Systems, Inc., May 22 ,1996, pp. 1–7.

Prospectus of Heartport, Apr. 25, 1996, pp. 1–64, F1–F15.

Robert J. Gardner, et al.,*An Experimental Anatomic Study of Indirect Myocardial Revascularization*, Journal of Surgical Research, vol. 11, No. 5, pp. 243–247 (May 1971).

Roque Pifarre, M.D., et al. *Myocardial Revascularization from the Left Ventricle: A Physiologic Impossibility*, 19 Surgical Forum 157–159 (1968).

Stuart W. Jamieson, *Aortocoronary Saphenous Vein Bypass Grafting*, in Rob & Smith's Operative Surgery: Cardiac Surgery 454–470 (Stuart W. Jamieson & Norman E. Shumway, eds. , 4th ed. 1986).

Tea E. Acuff, M.D. et al., *Minimally Invasive Coronary Artery Bypass Grafting*, 61 Annals of Thoracic Surgery 135–137 (1996).

Toshiyuki Beppu, ME et al.,*A Computerized Control System for Cardiopulmonary Bypass*, 109 J. Thoracic & Cardiovascular Surgery 428–438 (Mar. 1995).

Ulrich Sigwart, *An Overview of Intravascular Stents: Old and New*, in 2 Topol's Textbook of Interventional Cardiology 803–815 (Eric J. Topol ed., 2nd ed. 1994).

Vineberg, M.D., et al., *Treatment of Acute Myocardial Infarction by Endocardial Resection*, 57 Surgery 832–835 (Jun. 1965).

Wanpen Vongpatanasin, M.D. et al., *Prosthetic Heart Valves*, 335 N.E.J.M. 407–416 (Aug. 8, 1996).

* cited by examiner

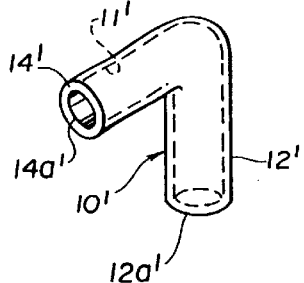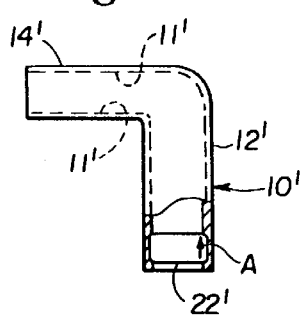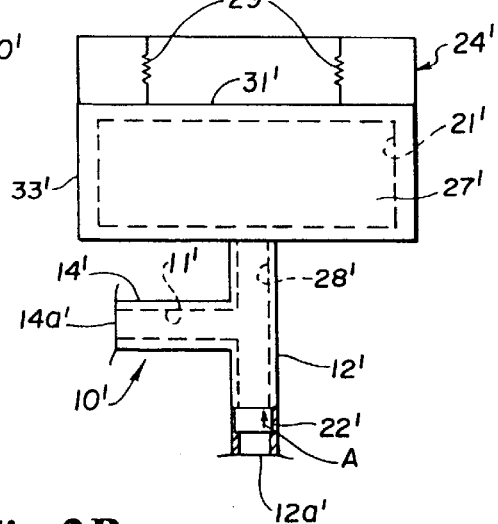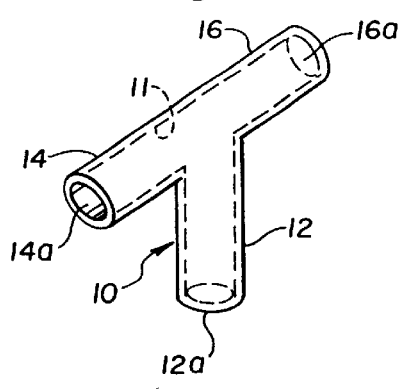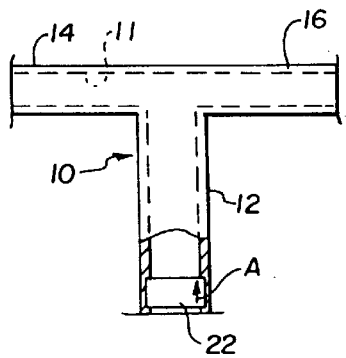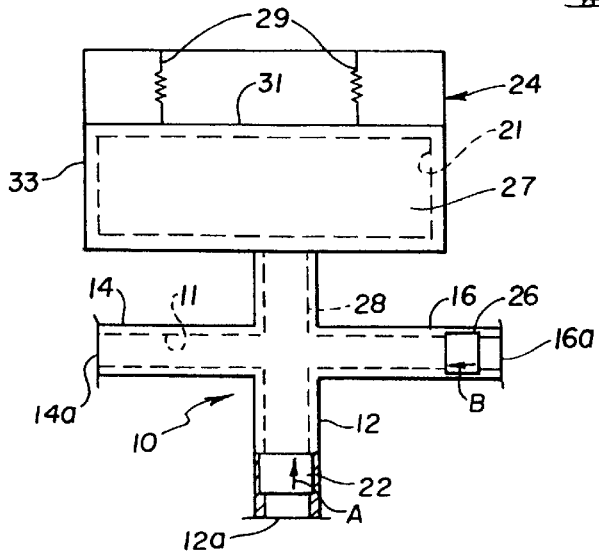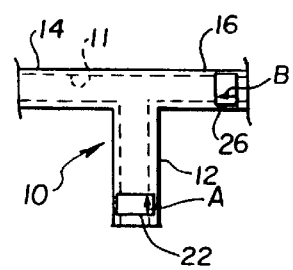

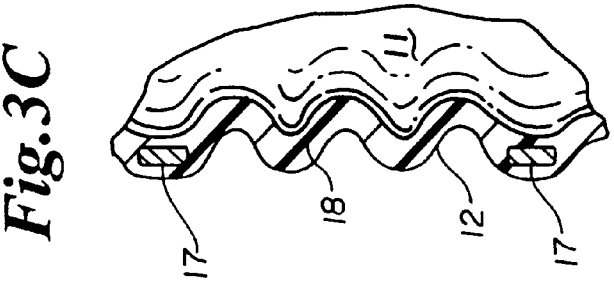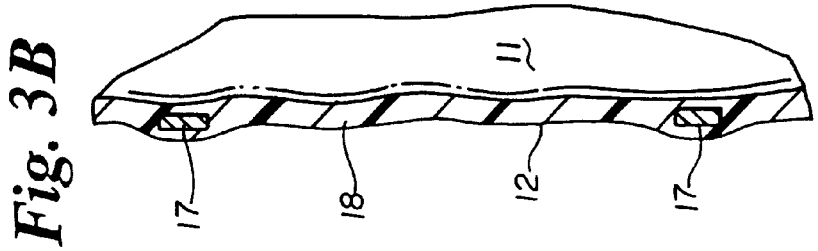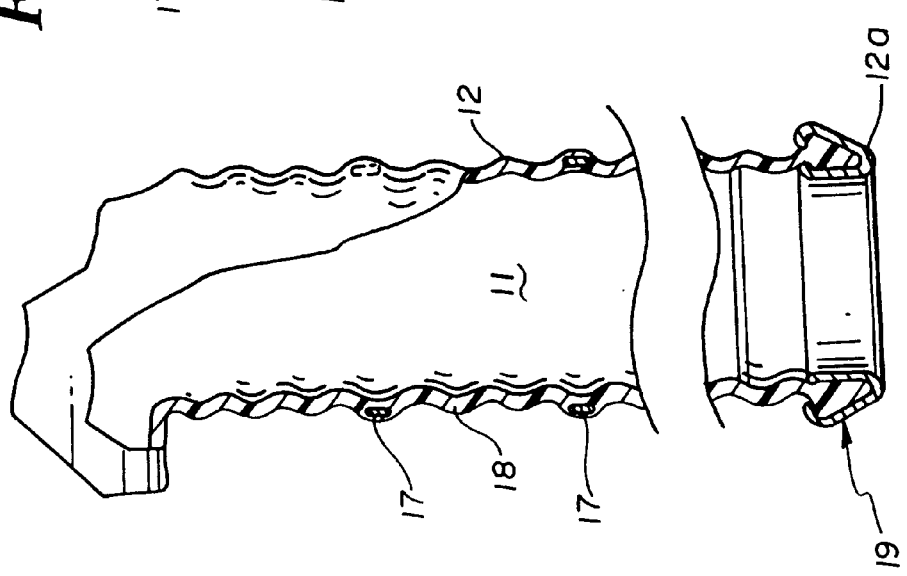

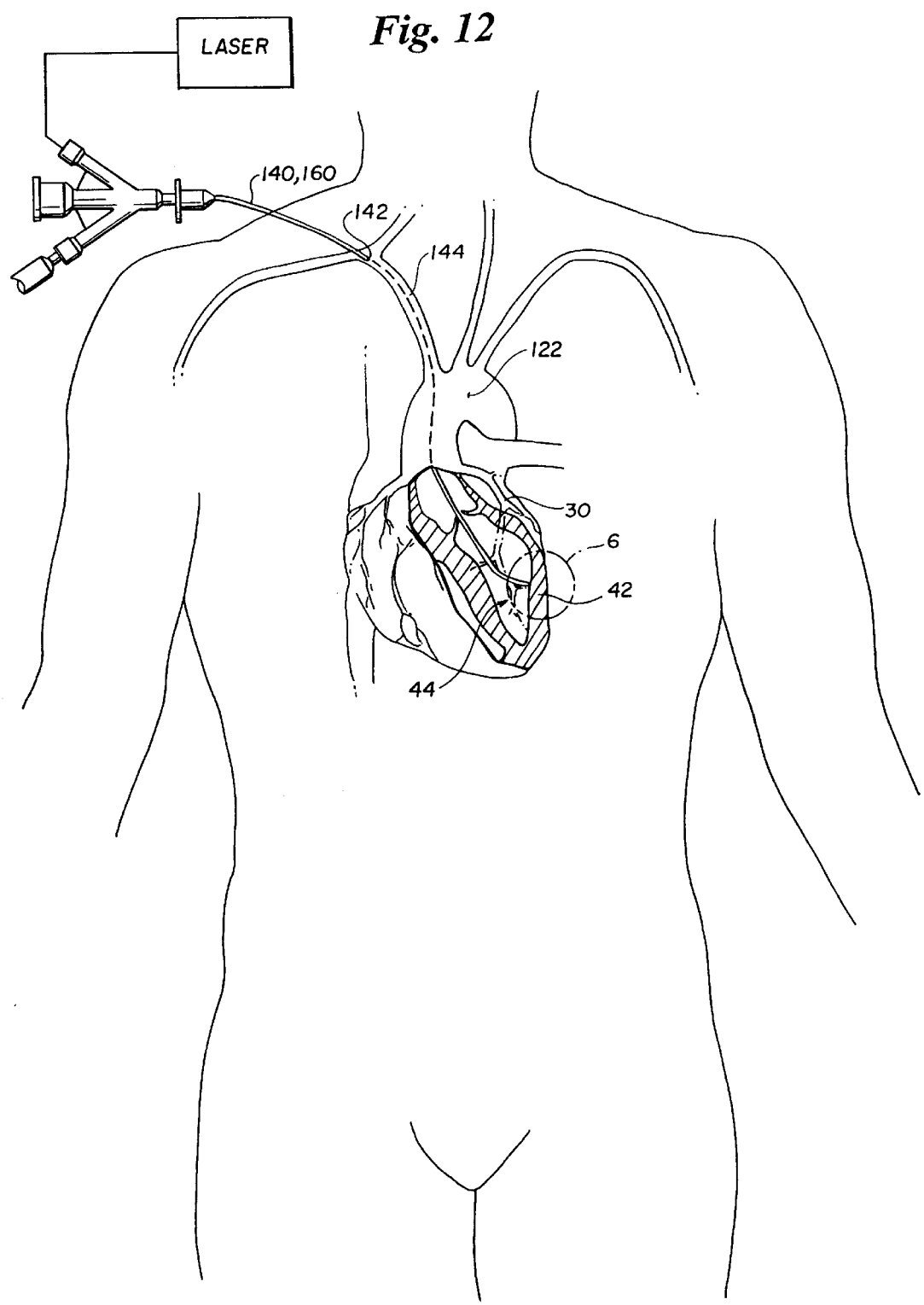

METHOD AND APPARATUS FOR REVASCULARIZING A CORONARY VESSEL WITH AN IMPLANT HAVING A TAPERED MYOCARDIAL LEG

I. CROSS-REFERENCE TO RELATED APPLICATIONS

The present application is a continuation of U.S. Ser. No. 09/326,819, filed Jun. 7, 1999, which issued as U.S. Pat. No. 6,454,794 on Sep. 24, 2002, which is a divisional of U.S. Ser. No. 08/882,397, filed Jun. 25, 1997, which issued as U.S. Pat. No. 5,944,019 on Aug. 31, 1999, which is a continuation-in-part of U.S. Ser. No. 08/689,773, filed Aug. 13, 1996, which issued as U.S. Pat. No. 5,755,682 on May 26, 1998.

II. BACKGROUND OF THE INVENTION

1. Field of the Invention

The present invention relates generally to a method and apparatus for performing a coronary artery bypass procedure. More particularly, the present invention performs a coronary artery bypass by providing a direct flow path from a heart chamber to the coronary artery. The present invention is suitable for a number of approaches including an open-chest approach (with and without cardiopulmonary bypass), a closed-chest approach under direct viewing and/or indirect thoracoscopic viewing (with and without cardiopulmonary bypass), and an internal approach through catheterization of the heart and a coronary arterial vasculature without direct or indirect viewing (with and without cardiopulmonary bypass).

2. Description of the Prior Art

A. Coronary Artery Disease

Coronary artery disease is the leading cause of premature death in industrialized societies. The mortality statistics tell only a portion of the story. Many who survive face prolonged suffering and disability.

Arteriosclerosis is "a group of diseases characterized by thickening and loss of elasticity of arterial walls." DORLAND's ILLUSTRATED MEDICAL DICTIONARY 137 (27th ed. 1988). Arteriosclerosis "comprises three distinct forms: atherosclerosis, Monckeberg's arteriosclerosis, and arteriolosclerosis." Id.

Coronary artery disease has been treated by a number of means. Early in this century, the treatment for arteriosclerotic heart disease was largely limited to medical measures of symptomatic control. Evolving methods of diagnosis, coupled with improving techniques of post-operative support, now allow the precise localization of the blocked site or sites and either their surgical re-opening or bypass.

B. Angioplasty

The re-opening of the stenosed or occluded site can be accomplished by several techniques. Angioplasty, the expansion of areas of narrowing of a blood vessel, is most often accomplished by the intravascular introduction of a balloon-equipped catheter. Inflation of the balloon causes mechanical compression of the arteriosclerotic plaque against the vessel wall.

Alternative intravascular procedures to relieve vessel occlusion include atherectomy, which results in the physical desolution of plaque by a catheter equipped with a removal tool (e.g., a cutting blade or high-speed rotating tip). Any of these techniques may or may not be followed by the placement of a mechanical support (i.e., a stent) which physically holds open the artery.

Angioplasty, and the other above-described techniques (although less invasive than coronary artery bypass grafting) are fraught with a correspondingly greater failure rate due to intimal proliferation. Contemporary reports suggest re-stenosis is realized in as many as 25 to 55 percent of cases within 6 months of successful angioplasty. See Bojan Cercek et al., 68 AM. J. CARDIOL. 24C–33C (Nov. 4, 1991). It is presently believed stenting can reduce the re-stenosis rate.

A variety of approaches to delay or prevent re-blockage have evolved. One is to stent the site at the time of balloon angioplasty. Another is pyroplasty, where the balloon itself is heated during inflation. As these alternative techniques are relatively recent innovations, it is too early to tell just how successful they will be in the long term. However, because re-blockage necessitates the performance of another procedure, there has been renewed interest in the clearly longer-lasting bypass operations.

C. Coronary Artery Bypass Grafting i. Outline of Procedure

The traditional open-chest procedure for coronary artery bypass grafting requires an incision of the skin anteriorly from nearly the neck to the navel, the sawing of the sternum in half longitudinally, and the spreading of the ribcage with a mechanical device to afford prolonged exposure of the heart cavity. If the heart chamber or a vessel is opened, a heart-lung, or cardiopulmonary bypass, procedure is usually necessary.

Depending upon the degree and number of coronary vessel occlusions, a single, double, triple, or even greater number of bypass procedures may be necessary. Often each bypass is accomplished by the surgical formation of a separate conduit from the aorta to the stenosed or obstructed coronary artery at a location distal to the diseased site.

ii. Limited Number of Available Grafts

The major obstacles to coronary artery bypass grafting include both the limited number of vessels that are available to serve as conduits and the skill required to effect complicated multiple vessel repair. Potential conduits include the two saphenous veins of the lower extremities, the two internal thoracic (mammary) arteries under the sternum, and the single gastroepiploic artery in the upper abdomen.

Newer procedures using a single vessel to bypass multiple sites have evolved. This technique has its own inherent hazards. When a single vessel is used to perform multiple bypasses, physical stress (e.g., torsion) on the conduit vessel can result. Such torsion is particularly detrimental when this vessel is an artery. Unfortunately, attempts at using artificial vessels or vessels from other species (xenografts), or other non-related humans (homografts) have been largely unsuccessful. See LUDWIG K. VON SEGESSER, ARTERIAL GRAFTING FOR MYOCARDIAL REVASCULARIZATION: INDICATIONS, SURGICAL TECHNIQUES AND RESULTS 38–39 (1990)

While experimental procedures transplanting alternative vessels continue to be performed, in general clinical practice, there are five vessels available to use in this procedure over the life of a particular patient. Once these vessels have been sacrificed or affected by disease, there is little or nothing that modern medicine can offer. It is unquestionable that new methods, not limited by the availability of such conduit vessels, are needed.

iii. Trauma of Open Chest Surgery

In the past, the normal contractions of the heart have usually been stopped during suturing of the bypass vasculature. This can be accomplished by either electrical stimulation which induces ventricular fibrillation, or through the use of certain solutions, called cardioplegia, which chemically alter the electrolyte milieu surrounding cardiac muscles and arrest heart activity.

Stoppage of the heart enhances visualization of the coronary vessels and eliminates movement of the heart while removing the need for blood flow through the coronary arteries during the procedure. This provides the surgeon with a "dry field" in which to operate and create a functional anastomosis.

After the coronary artery bypass procedure is completed, cardioplegia is reversed, and the heart electrically stimulated if necessary. As the heart resumes the systemic pumping of blood, the cardiopulmonary bypass is gradually withdrawn. The separated sternal sections are then re-joined, and the overlying skin and saphenous donor site or sites (if opened) are sutured closed.

The above-described procedure is highly traumatic. Immediate post-operative complications include infection, bleeding, renal failure, pulmonary edema and cardiac failure. The patient must remain intubated and under intensive post-operative care. Narcotic analgesia is necessary to alleviate the pain and discomfort.

iv. Post-operative Complications

Once the immediate post-surgical period has passed, the most troubling complication is bypass vessel re-occlusion. This has been a particular problem with bypass grafting of the left anterior descending coronary artery when the saphenous vein is employed.

Grafting with the internal thoracic (internal mammary) artery results in a long-term patency rate superior to saphenous vein grafts. This is particularly the case when the left anterior descending coronary artery is bypassed. Despite this finding, some cardiothoracic surgeons continue to utilize the saphenous vein because the internal thoracic artery is smaller in diameter and more fragile to manipulation. This makes the bypass more complex, time-consuming, and technically difficult. Additionally, there are physiological characteristics of an artery (such as a tendency to constrict) which increase the risk of irreversible damage to the heart during the immediate period of post-surgical recovery.

Once the patient leaves the hospital, it may take an additional five to ten weeks to recover completely. There is a prolonged period during which trauma to the sternum (such as that caused by an automobile accident) can be especially dangerous. The risk becomes even greater when the internal thoracic artery or arteries, which are principle suppliers of blood to the sternum, have been ligated and employed as bypass vessels.

v. Less Invasive Procedures

Due to the invasive nature of the above technique, methods have been devised which employ contemporary thoracoscopic devices and specially-designed surgical tools to allow coronary artery bypass grafting by closed-chest techniques. While less invasive, all but the most recent closed-chest techniques still require cardiopulmonary bypass, and rely on direct viewing by the surgeon during vascular anastomoses.

These methods require a very high level of surgical skill together with extensive training. In such situations, the suturing of the bypassing vessel to the coronary artery is performed through a space created in the low anterior chest wall by excising the cartilaginous portion of the left fourth rib. Also, as they continue to rely on the use of the patient's vessels as bypass conduits, the procedures remain limited as to the number of bypasses which can be performed. Because of these issues, these methods are not yet widely available.

vi. Objectives for Improved Bypass Procedures

In view of the above, it is desirable to provide other methods by which adequate blood flow to the heart can be re-established and which do not rely on the transposition of a patient's own arteries or veins. Preferably, such methods will result in minimal tissue injury.

While the attainment of the foregoing objectives through an open chest procedure would, by themselves, be a significant advance, it is also desirable if such methods would also be susceptible to surgical procedures which do not require opening of the chest by surgical incision of the overlying skin and the division of the sternum. Such methods would not require surgical removal of cartilage associated with the left fourth rib, would not require the surgical transection of one or both internal thoracic arteries, would not require the surgical incision of the skin overlying one or both lower extremities, and would not require the surgical transection and removal of one or both saphenous veins. In both an open and closed chest approach, it is also be desirable if such methods could be performed without stoppage of the heart and without cardiopulmonary bypass. However, attainment of the foregoing objectives in a procedure requiring cardiopulmonary bypass would still be a significant advance in the art.

vii. References for Prior Art Techniques

The conventional surgical procedures (such as those described above) for coronary artery bypass grafting using saphenous vein or internal thoracic artery via an open-chest approach have been described and illustrated in detail. See generally Stuart W. Jamieson, *Aortocoronary Saphenous Vein Bypass Grafting*, in ROB & SMITH's OPERATIVE SURGERY: CARDIAC SURGERY, 454–470 (Stuart W. Jamieson & Norman E. Shumway eds., 4th ed. 1986); LUDWIG K. VON SEGESSER, ARTERIAL GRAFTING FOR MYOCARDIAL REVASCULARIZATION: INDICATIONS, SURGICAL TECHNIQUES AND RESULTS 48–80 (1990). Conventional cardiopulmonary bypass techniques are outlined in Mark W. Connolly & Robert A. Guyton, *Cardiopulmonary Bypass Techniques*, in HURST'StHE HEART 2443–450 (Robert C. Schlant & R. Wayne Alexander eds., 8th ed. 1994). Coronary artery bypass grafting utilizing open-chest techniques but without cardiopulmonary bypass is described in Enio Buffolo et al., *Coronary Artery Bypass Grafting Without Cardiopulmonary Bypass*, 61 ANN. THORAC. Surg. 63–66 (1996).

Some less conventional techniques (such as those described above) are performed by only a limited number of appropriately skilled practitioners. Recently developed techniques by which to perform a coronary artery bypass graft utilizing thoracoscopy and minimally-invasive surgery, but with cardiopulmonary bypass, are described and illustrated in Sterman et al., U.S. Pat. No. 5,452,733 (1995). An even more recent coronary artery bypass procedure employing thoracoscopy and minimally-invasive surgery, but without cardiopulmonary bypass, is described and illustrated by Tea E. Acuff et al., *Minimally Invasive Coronary Artery Bypass Grafting*, 61 ANN. THORAC. SURG. 135–37 (1996).

D. Bypass With Direct Flow From Left Ventricle

1. Summary of Procedures

Certain methods have been proposed to provide a direct blood flow path from the left ventricle directly through the heart wall to the coronary artery. These are described in U.S. Pat. No. 5,429,144 dated Jul. 4, 1995; U.S. Pat. No. 5,287,861 dated Feb. 22, 1994; and U.S. Pat. No. 5,409,019 dated Apr. 25, 1995 (all to Wilk). All of these techniques include providing a stent in the heart wall to define a direct flow path from the left ventricle of the heart to the coronary artery.

As taught in each of the above-referenced patents, the stent is closed during either systole or diastole to block return flow of blood from the coronary artery during the heart's cycle. For example, the '861 patent teaches a stent which collapses to a closed state in response to heart muscle contraction during systole. The '019 patent (particularly FIGS. 7A and 7B) teaches a rigid stent (i.e., open during systole) with a one-way valve which closes during diastole to block return flow of blood from the coronary artery.

ii. Problems

The interruption of blood flow during either diastole or systole is undesirable since such interruption can result in areas of stagnant or turbulent blood flow. Such areas of stagnation can result in clot formation which can result in occlusion or thrombi breaking lose. Such thrombi can be carried to the coronary arteries causing one or more areas of cardiac muscle ischemia (myocardial infarction) which can be fatal. Further, the teachings of the aforementioned patents direct blood flow with a substantial velocity vector orthogonal to the axis of the coronary artery. Such flow can damage the wall of the coronary artery.

Providing direct blood flow from the left ventricle of the coronary artery has been criticized. For example, Munro et al., *The Possibility of Myocardial Revascularization By Creation of a Left Ventriculocoronary Artery Fistula*, 58 Jour. Thoracic and Cardiovascular Surgery, 25–32 (1969) shows such a flow path in FIG. 1. Noting a fall in coronary artery flow and other adverse consequences, the authors concluded "that operations designed to revascularize the myocardium direct from the cavity of the left ventricle make the myocardium ischemic and are unlikely to succeed." Id at 31.

Notwithstanding the foregoing problems and scholarly criticism, and as will be more fully described, the present invention is directed to an apparatus and method for providing a direct blood flow path from a heart chamber to a coronary artery downstream of an obstruction. Counter to the teachings of the prior art, the present invention provides substantial net blood flow to the coronary artery.

E. Additional Techniques

Methods of catheterization of the coronary vasculature, techniques utilized in the performance of angioplasty and atherectomy, and the variety of stents in current clinical use have been summarized. See generally Bruce F. Waller & Cass A. Pinkerton, *The Pathology of Interventional Coronary Artery Techniques and Devices*, in 1 TOPOL'S TEXTBOOK OF INTERVENTIONAL CARDIOLOGY 449–476 (Eric J. Topol ed., 2nd ed. 1994); see also David W. M. Muller & Eric J. Topol, *Overview of Coronary Athrectomy*, in 1 TOPOL'S TEXTBOOK OF INTERVENTIONAL CARDIOLOGY at 678–684; see also Ulrich Sigwart,*An Overview of Intravascular Stents: Old & New*, in 2 TOPOL'S TEXTBOOK OF INTERVENTIONAL CARDIOLOGY at 803–815.

Direct laser canalization of cardiac musculature (as opposed to canalization of coronary artery feeding the cardiac musculature) is described in Peter Whittaker et al., *Transmural Channels Can Protect Ischemic Tissue: Assessment of Long-term Myocardial Response to Laser-and Needle-Made Channels*, 94(1) CIRCULATION 143–152 (Jan. 1, 1996). Massimo et al., *Myocardial Revascularization By a New Method of Carrying Blood Directly From The Left Ventricular Cavity Into The Coronary Circulation*, 34 Jour. Thoracic Surgery 257–264 (1957) describes a T-shaped tube placed within the ventricular wall and protruding into the cavity of the left ventricle. Also, Vineberg et al., *Treatment of Acute Myocardial Infarction By Endocardial Resection*, 57 Surgery 832–835 (1965) teaches forming a large opening between the left ventricular lumen and the sponge-like network of vessels lying within the myocardium.

III. SUMMARY OF THE INVENTION

The present invention relates to a method for revascularizing a coronary vessel with a conduit through the heart wall having a diameter transition in the myocardial leg, wherein blood flow is in the direction of transition from larger to smaller diameter. The present invention further relates to revascularizing a coronary vessel using an implant with a transmyocardial leg having a maximum cross-sectional area proximate a first end, and inserting the first end through the myocardium into a heart chamber so that the implant directs blood flow into the coronary vessel. The present invention also relates to a transmyocardial implant with a myocardial leg including point of minimum diameter and a first end with a larger diameter, and a vessel leg in fluid communication with the myocardial leg.

IV. BRIEF DESCRIPTION OF THE DRAWINGS

FIG. 1A is a right, front and top perspective view of an L-shaped conduit for use in the present invention;

FIG. 1B is a side elevation view of the apparatus of FIG. 1A shown partially in section to reveal an optional bi-directional flow regulator located in a lumen of an anchor arm of the conduit;

FIG. 1C is a side elevation view of a conduit similar to that of FIG. 1A showing the addition of a capacitance pressure reservoir as an alternative embodiment;

FIG. 2A is a right, front and top perspective view of a T-shaped conduit according to the present invention;

FIG. 2B is a side elevation view of the conduit of FIG. 2A shown partially in section to reveal an optional bi-directional flow regulator located in a lumen of an anchor arm of the conduit;

FIG. 2C is a side elevation view of the conduit of FIG. 2A shown partially in section to reveal one optional bi-directional flow regulator located in the lumen of the anchor arm of the conduit, and another optional bi-directional flow regulator located in an intracoronary arm of the conduit;

FIG. 2D is a side elevation view of a conduit similar to that of FIG. 2A showing the addition of a capacitance pressure reservoir as an alternative embodiment;

FIG. 3A is a partial side elevation view of a conduit similar to that of FIGS. 1A and 2A shown partially in section to reveal a flexible anchor arm with rigid rings ensheathed in a flexible covering as an alternative embodiment;

FIG. 3B is a partial side elevation view of a conduit similar to that of FIG. 3A shown in section in an extended form;

FIG. 3C is a partial side elevation view of a conduit similar to that of FIG. 3A shown in section in a compressed form;

FIG. 12 is a schematic illustration with the heart in partial cutaway of the use of an endovascular catheter to catheterize the patient's left ventricle.

V. DESCRIPTION OF THE PREFERRED EMBODIMENT

With reference now to the various drawing figures in which identical elements are numbered identically throughout, a description of the preferred embodiment of the present invention and various alternative embodiments will now be provided.

A. Detailed Summary of the Preferred Embodiment

The invention departs from the traditional bypass approach. Rather then providing an alternative pathway for blood to flow from an aorta to a coronary artery, the invention provides a blood flow path leading directly from a chamber of a heart to a coronary artery at a site downstream from the stenosis or occlusion. Unlike U.S. Pat. Nos. 5,429,144; 5,287,861 and 5,409,019 and contrary to the teachings of these patents, the ventricular-to-coronary artery blood flow path remains open during both diastole and systole. The surgical placement of the apparatus of the present invention establishes this alternative pathway. Also, and as will be more fully described, the invention includes means for protecting the coronary artery from direct impingement of high velocity blood flow.

While the invention will be described in multiple embodiments and with the description of various surgical procedures for practicing the invention, it will be appreciated that the recitation of such multiple embodiments is done for the purpose of illustrating non-limiting examples of multiple forms which the present invention may take.

The presently preferred embodiment is illustrated in FIG. 1A as an L-shaped conduit 10' with an intracoronary arm 14' to reside in the coronary artery (and opening downstream of an occlusion). The conduit 10' has an anchor arm 12' extending through the heart wall with an opening 12a' in communication with the interior of the left ventricle.

While various minimally invasive surgical procedures are described with respect to alternative embodiments, the presently preferred embodiment places the conduit 10' into a coronary artery through an open-chest approach to be described in greater detail with reference to FIGS. 4–9. While minimally invasive procedures are desirable, an open chest procedure is presently preferred due to the already large number of physicians trained and skilled in such procedures thus making the benefits of the present invention more rapidly available to patients who currently lack effective treatment.

While the various embodiments (including the presently preferred embodiment of FIG. 1A) will be described in greater detail, a preliminary description of the invention and its method of use will now be given with reference to FIG. 21 to facilitate an understanding of a detailed description of the invention and the alternate embodiments.

Figure 21:
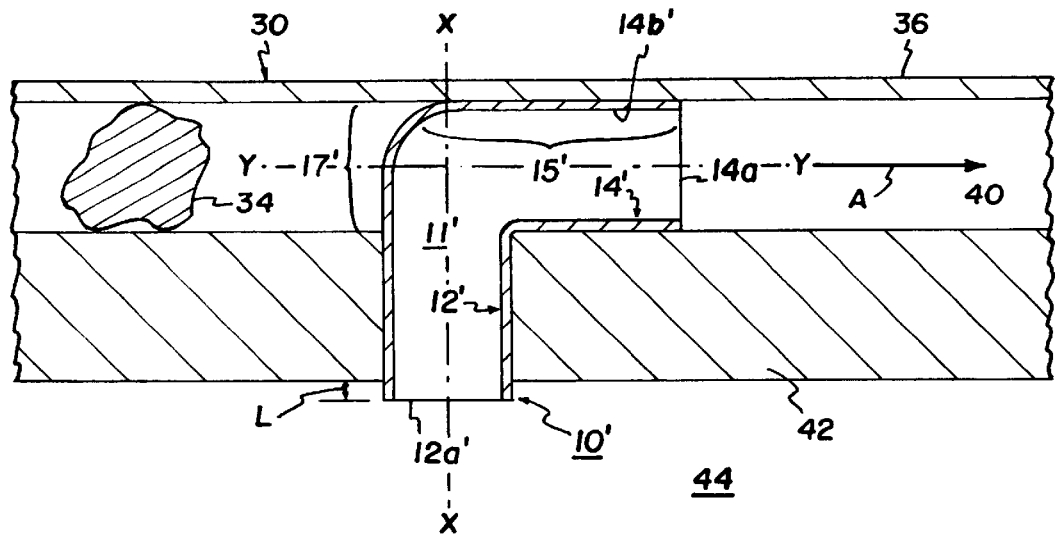
FIG. 21 is a schematic longitudinal cross-sectional view of the conduit of FIG. 1A in place in a coronary artery.

FIG. 21 is a schematic cross-sectional view of a conduit 10' of FIG. 1A placed within a coronary artery 30. Coronary artery 30 has a lower surface 40 residing against an external surface of a heart wall 42 surrounding the left ventricle 44.

The wall 36 of the artery 30 defines an artery lumen 48 through which blood flows in the direction of arrow A. In the view of FIG. 21, an obstruction 34 is shown within the lumen 48. The obstruction 34 acts to reduce the volume of blood flow along the direction of arrow A.

The conduit 10' is a rigid, L-shaped tube having an anchor arm 12' with a longitudinal axis X—X and an opening 12a' at an axial end. The conduit 10' may be any suitable device (e.g., rigid tube, lattice stent, etc.) for defining and maintaining a fluid pathway during contraction of the heart.

The conduit 10' has an intracoronary arm 14' with a longitudinal axis Y—Y and an opening 14a' at an axial end. Both of arms 12', 14' are cylindrical in shape and define a continuous blood flow pathway 11' from opening 12a' to opening 14a'.

The axes X—X and Y—Y are perpendicular in a preferred embodiment. Alternatively, the axes X—X, Y—Y could define an angle greater than 90° to provide a less turbulent blood flow from arm 12' to arm 14'.

The conduit 10' is positioned for the anchor arm 12' to pass through a preformed opening 50 in the heart wall 42 and extending from the lower surface 40 of the coronary artery 30 into the left ventricle 44. The opening 12a' is in blood flow communication with the interior of the left ventricle 44 so that blood may flow from the left ventricle 44 directly into path 11'. The arm 14' is coaxially aligned with the coronary artery 30 and with the opening 14a' facing downstream (i.e., in a direction facing away from obstruction 34).

Blood flow from opening 12a' passes through the pathway 11' and is discharged through opening 14a' into the lumen 48 of the coronary artery 30 downstream of the obstruction 34. The outer diameter of arm 14a' is approximate to or slightly less than the diameter of the lumen 48.

The axial length of the anchor arm 12' is preferably greater than the thickness of the heart wall 42 such that a length L protrudes beyond the interior surface of the heart wall 42 into the left ventricle 44. Preferably, the length L of penetration into the left ventricle 44 is about 1–3 millimeters in order to prevent tissue growth and occlusions over the opening 12a'.

In addition to directing blood flow downstream in the direction of arrow A, the arm 14' holds the conduit 10' within the coronary artery 30 to prevent the conduit 10' from otherwise migrating through the preformed opening 50 and into the left ventricle 44. Additionally, an upper wall 14b' of arm 14' defines a region 15' against which blood flow may impinge. Stated differently, in the absence of an arm 14' or region 15', blood flow would pass through the anchor arm 12' and impinge directly against the upper wall 36 of the coronary artery 30. High velocity blood flow could damage the wall 36, as will be more fully described, resulting in risk to the patient.

Figure 23:
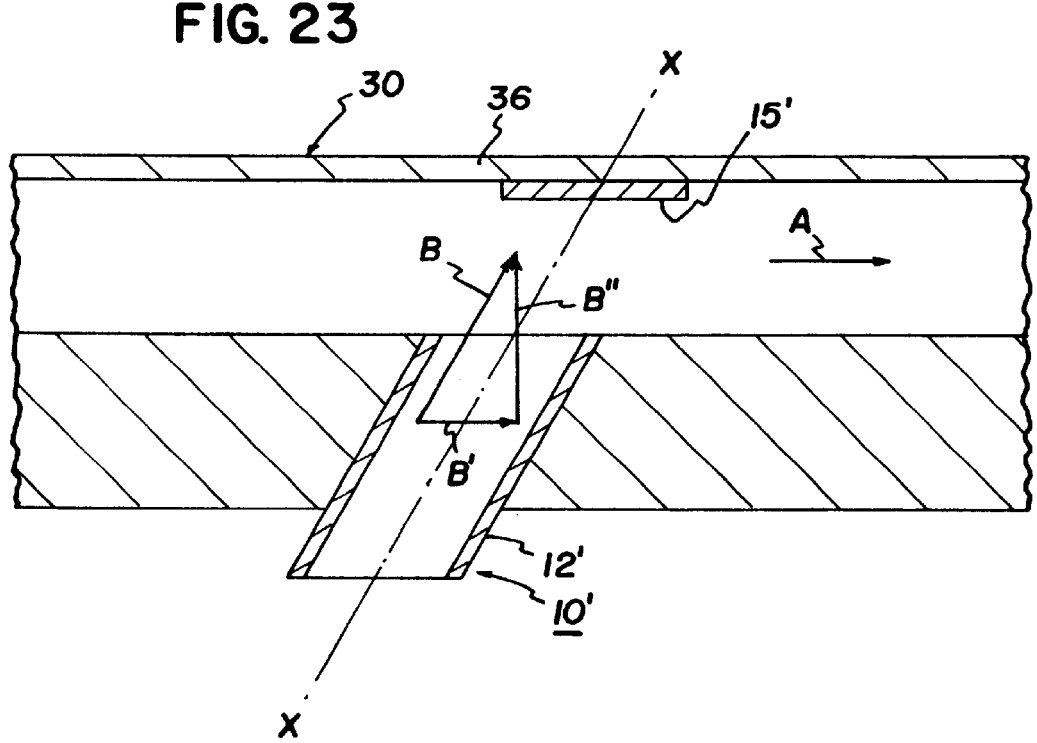
FIG. 23 is a schematic longitudinal cross-sectional view of a conduit in place in a coronary artery illustrating a deflecting shield to protect the coronary artery.

The region 15' acts as a shield to protect the coronary artery 30 from such blood flow and to redirect the blood flow axially out of opening 14a' into the coronary artery 30. This is schematically illustrated in FIG. 23. For ease of illustration, the axis X—X of the anchor arm 12' is shown at a non-orthogonal angle with respect to the direction A of blood flow in the coronary artery 30 (axis X—X may be either orthogonal or non-orthogonal to direction A). The vector B of blood flow from the anchor arm 12' has a vector component B' parallel to blood flow A and a vector component B" perpendicular to direction A. The region 15' is positioned between the wall 36 and anchor arm 12' to prevent the blood flow B with high vector component B" from impinging upon wall 36. The blood flow deflected off region 15' has a reduced vector component perpendicular to flow direction A and reduced likelihood of damage to the coronary artery 30. The region 15' may be a portion of an intracoronary arm 14' or the arm 14' may be eliminated with the region 15' being an axially spaced extension from arm 12' or a separate shield surgically positioned within the coronary artery.

A portion 17' of the anchor arm 12' extends from the lower surface 40 of the coronary artery 30 and through the lumen 48 to the upper surface 36 to block the cross-section of the coronary artery upstream from opening 14a'. The region 17' acts as a barrier to impede or prevent any dislodged portions of the obstruction 34 from passing the conduit 10' and flowing downstream through the coronary artery 30.

The present invention maintains blood flow through the conduit 10' during both diastole and systole. Therefore, while the net blood flow is in the direction of arrow A, during diastole, blood will flow in a direction opposite of that of arrow A.

Figure 22:
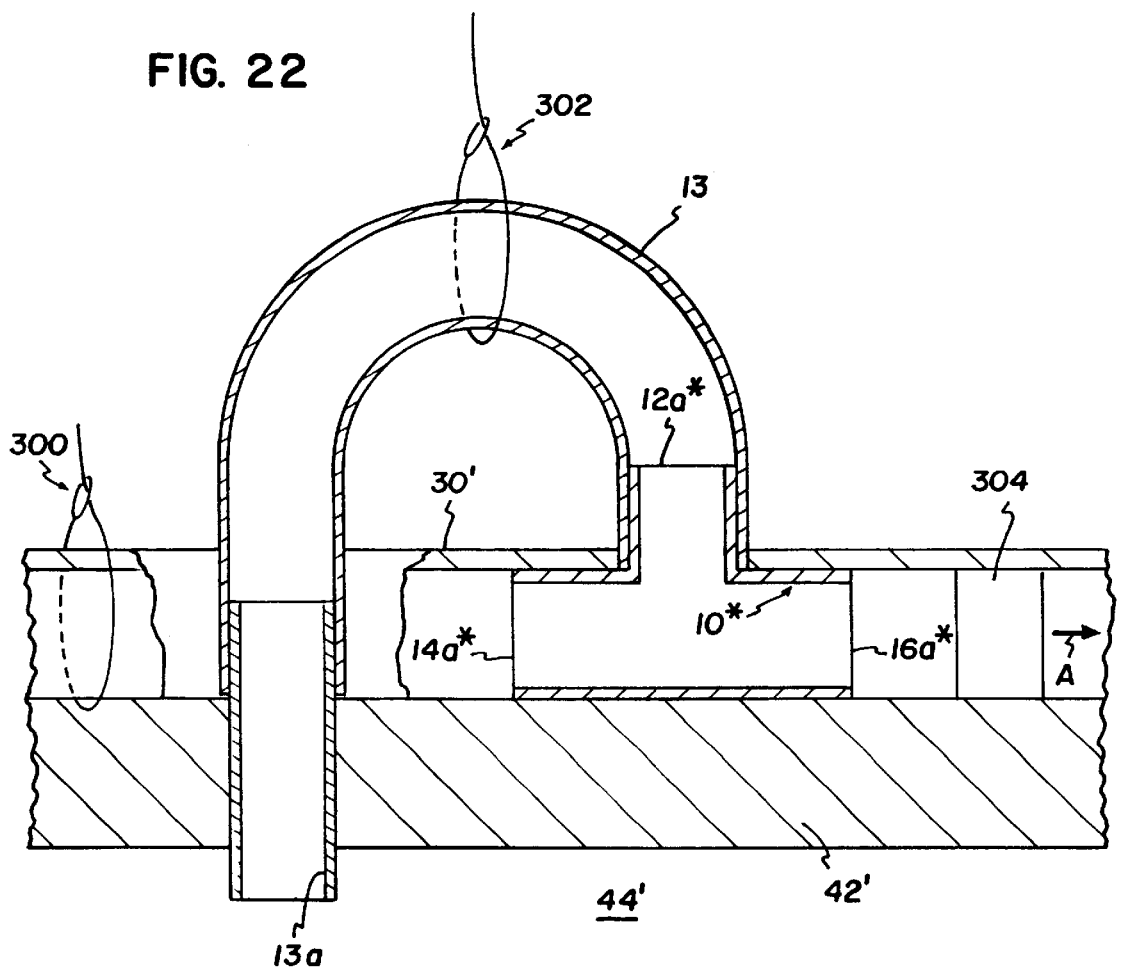
FIG. 22 is a schematic longitudinal cross-sectional view of a test conduit for animal testing of the invention.

The constantly open pathway 11' results in a net flow in the direction of arrow A which is extraordinarily high and sufficient to reduce or avoid patient symptoms otherwise associated with an obstruction 34. Specifically, certain aspects of the apparatus and method of the present invention have been preliminary tested in animal studies. FIG. 22 schematically illustrates the tests as the placement of a test conduit 10* in the coronary artery 30' of a pig. For purposes of the tests, a stainless steel T-shaped conduit 10* is used having aligned openings 14a*, 16a* positioned within the coronary artery 30' and with a third opening 12a* protruding 90° out of the coronary artery 30'. The conduit 10* has a uniform interior diameter of 3 millimeters to correspond in sizing with a 3 millimeter lumen of coronary artery 30'. The third opening 12a* is connected by a 3 millimeter conduit 13 to a 3 millimeter rigid Teflon (PTFE) sleeve 13a which was passed through the heart wall 42' into the left ventricle 44'. The conduit 13 and sleeve 13a do not pass through the coronary artery 30'.

In the view of FIG. 22, the direction of net blood flow is shown by arrow A. A first closure device in the form of a suture loop 300 surrounds the artery 30' adjacent the upstream opening 14a* of the conduit 10*. The loop 300 provides a means for closing the upstream opening 14a* by selectively constricting or opening the loop 300 to selectively open or block blood flow through the coronary artery 30'. The first loop 300 permits the test to simulate blockage of the coronary artery 30' upstream of the conduit 10*.

A flow meter 304 to measure volumetric flow of blood downstream of the conduit 10* is placed adjacent downstream opening 16a*. A second closure device 302 functioning the same as loop 300 is placed on conduit 13 to selectively open or close blood flow through conduit 13.

When the second device 302 is closed and the first device 300 is open, the conduit 10* simulates normal blood flow through a healthy coronary artery 30' and the normal blood flow can be measured by the flow measuring device 304. By opening second device 302 and closing the first device 300, the test conduit 10* can simulate the placement of a conduit such as that in FIG. 21 with an obstruction located on the upstream side of the conduit. The flow meter 304 can then measure flow of blood through the conduit 10* during both diastole and systole.

The results of the tests indicate there is a substantial net forward blood flow (i.e., volumetric forward flow less volumetric retro-flow) with the second device 302 remaining open during both diastole and systole and with the first device 300 closed to simulate an obstruction. Specifically, in the tests, net blood flows in excess of 80 percent of normal net forward blood flow were measured.

The amount of back flow through a conduit can be controlled without the need for providing a valve within the conduit. Conveniently referred to as flow "bias", a volumetric forward flow greater than a volumetric rearward flow can be manipulated through a variety of means including sizing of the interior diameter of the conduit, geometry of the conduit (e.g., taper, cross-sectional geometry and angle) and, as will be more fully discussed, structure to restrict rear flow relevant to forward flow.

The sizing of the interior diameter of the flow pathway 11' can be selected to minimize back flow. As will be more further discussed, the net flow increases with a reduction in the diameter as suggested by simulation modeling of flow through a conduit. One method in which shear rate and flow bias can be controlled is by providing a tapered diameter for a narrower diameter at opening 14a' than at opening 12a'. The selection of the conduit geometry (e.g., an angled anchor arm as shown in FIG. 23 or a tapered geometry as will be discussed with reference to FIG. 20) can be selected to modify the degree to which the conduit is biased to net forward flow (i.e., the conduit offers less resistance to forward flow than to retro-flow) without stopping or blocking retro-flow.

The substantial net blood flow measured in animal testing through the invention is extraordinarily high when compared to minimum acceptable levels of net blood flow following traditional bypass techniques (i.e., about 25 percent of normal net blood flow). Further, the results are counterintuitive and contradictory to the prior teachings of the art of U.S. Pat. Nos. 5,429,144; 5,287,861 and 5,409,919 and the afore-mentioned Munro et al. article. In addition, the present invention provides a conduit with a shielding area to prevent damaging impingement of blood flow directly onto the coronary artery wall as well as providing a blocking area to prevent the migration of debris from an obstruction to a location downstream of the conduit.

Having provided a summarized version of the present invention with reference to the schematic drawings of FIGS. 21 and 22, a more detailed description of the present invention as well as a detailed description of alternative embodiments and alternative surgical procedures will now be provided.

B. Embodiments with an Open Chest Approach

1. The Apparatus of the Present Invention for Use in the Open Chest Approach

As will be more fully described, the present invention places an apparatus for defining a blood flow conduit directly from a chamber of a heart to a coronary artery downstream of an occluded site. Before describing the surgical methods for placing such an apparatus, an apparatus of the present invention will be described. The apparatus of the present invention can be a variety of shapes or sizes, and is not meant to be limited as to size, shape, construction, material, or in any other way by the following examples in which a preferred embodiment is illustrated.

a. T-Shaped Device

With initial reference to FIGS. 2A, 2B, 2C, 2D and 2E, related embodiments of an apparatus according to the present invention are shown as a rigid T-shaped conduit 10 (a preferred L-shaped conduit 10' having already been summarized and to be later described in detail). The conduit 10 is hollow and includes two axially-aligned intracoronary arms 14, 16 terminating at open ends 14a, 16a. An anchor arm 12 (having an open end 12a) extends perpendicularly to arms 14, 16. The entire conduit 10 is hollow to define a blood flow conduit 11 providing blood flow communication between open ends 12a, 14a and 16a.

As will be more fully discussed, arms 14 and 16 are adapted to be placed and retained within a lumen of a coronary artery on a downstream side of an occlusion with open ends 14a, 16a in blood flow communication with the lumen. The anchor arm 12 is adapted to extend through and be retained in a heart wall (e.g., wall of the left ventricle) with the open end 12a in blood flow communication with blood within the chamber. When so placed, the conduit 10 defines a surgically-placed conduit establishing direct blood flow from the heart chamber to the artery. By "direct" it is meant that the blood flow does not pass through the aorta as occurs in traditional bypass procedures. The conduit 10 is sufficiently rigid such that it defines an open blood flow path during both diastole and systole.

b. Optional Forward Flow Bias

While unobstructed back flow is preferred, partially restricted back flow can be provided. As will be more fully described, back flow can be controlled by the geometry of the conduit. The following describes a presently less preferred alternative embodiment for controlling back flow.

FIG. 2B illustrates use of an optional bi-directional flow regulator 22 within the conduit 10 and positioned in anchor arm 12. The bi-directional flow regulator 22 permits unimpeded flow in the direction of arrow A (i.e., from open end 12a to open ends 14a, 16a) while permitting a reduced (but not blocked) reverse flow.

FIG. 2C illustrates the use of a first bi-directional flow regulator 22 as well as a second bi-directional flow regulator 26 in arm 16 near the open end 16a of the apparatus. The second bi-directional flow regulator 26 permits unimpeded blood flow in the direction of arrow B. The second bi-directional flow regulator 26 is used to permit a reduced (but not zero) back flow of blood in an upstream direction within the coronary artery. For example, the coronary artery may not be completely obstructed and may have a reduced flow past an obstruction. The use of the T-conduit 10 with axially aligned arms 14, 16 takes advantage of such reduced flow and supplements such flow with blood through anchor arm 12. As will be described, the conduit 10 is placed with the arms 14, 16 in the lumen of the artery with opening 16a positioned on the upstream side (i, nearest to, but still downstream of, the obstruction).

As indicated above, the flow regulator 22 is a bi-directional flow regulator. By this it is meant that the flow regulator 22 does not block flow of blood in any direction. Instead, the flow regulator 22 permits a first or maximum flow rate in one direction and a second or reduced flow rate in a second direction. The flow regulator is schematically illustrated in FIGS. 18A through 19C. In each of these embodiments, the arrow A indicates the direction of blood flow from the left ventricle to the coronary artery.

Figure 18A:
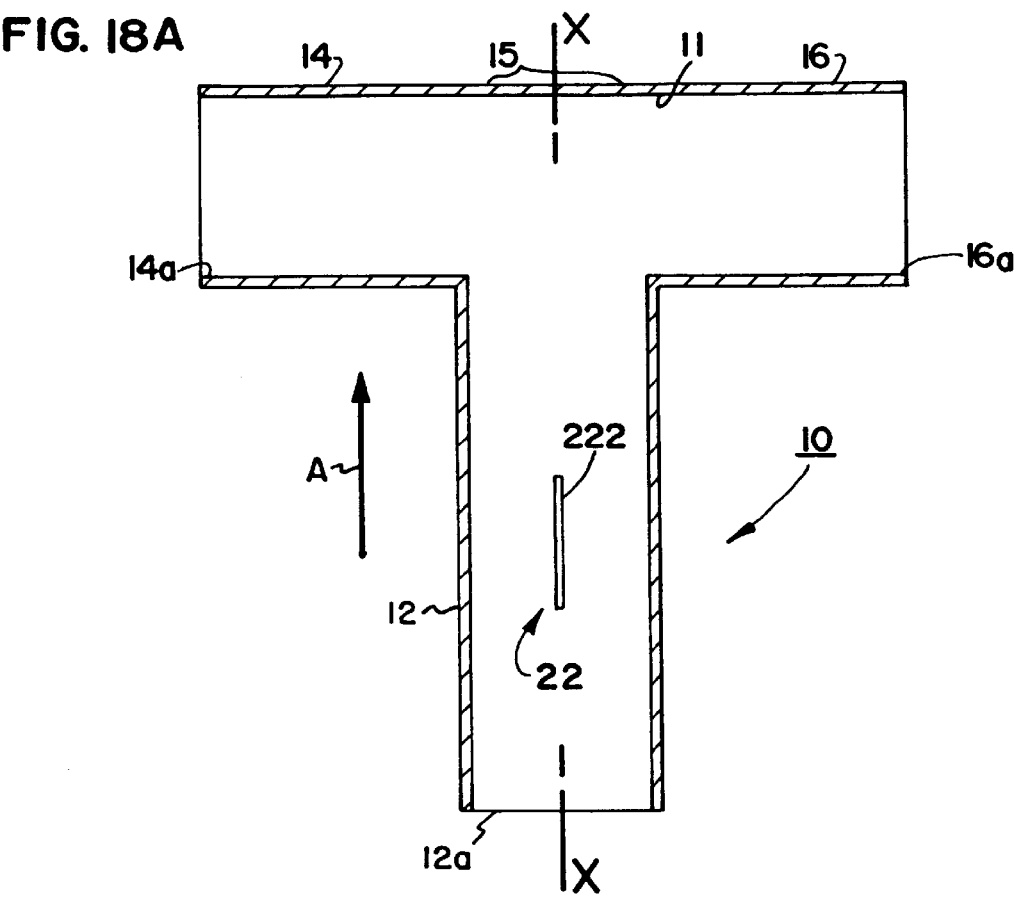
FIG. 18A is a schematic longitudinal cross-sectional view of a bi-directional flow regulator shown in a fill flow position.
Figure 18B:
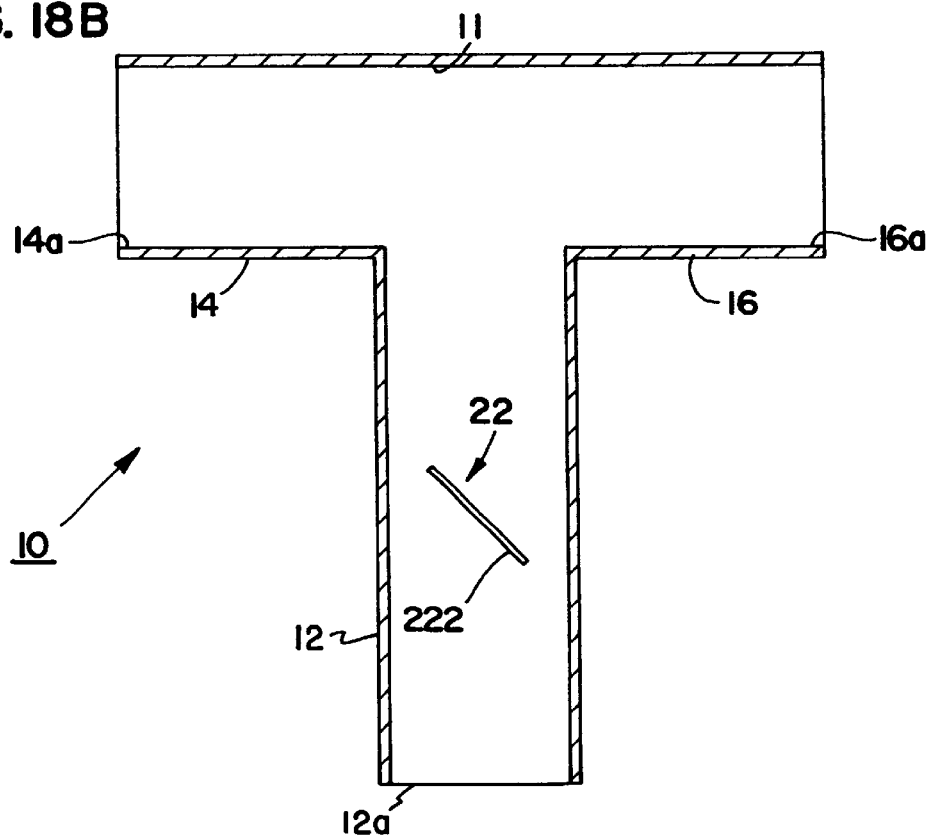
FIG. 18B is the view of FIG. 18A with the bi-directional flow regulator shown in a reduced flow position.
Figure 18C:
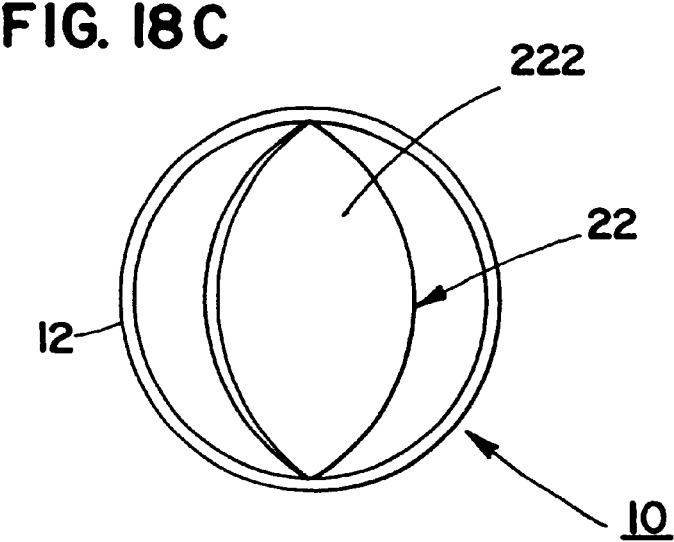
FIG. 18C is a transverse cross-sectional view of the bi-directional flow regulator of FIG. 18B.
Figure 19C:
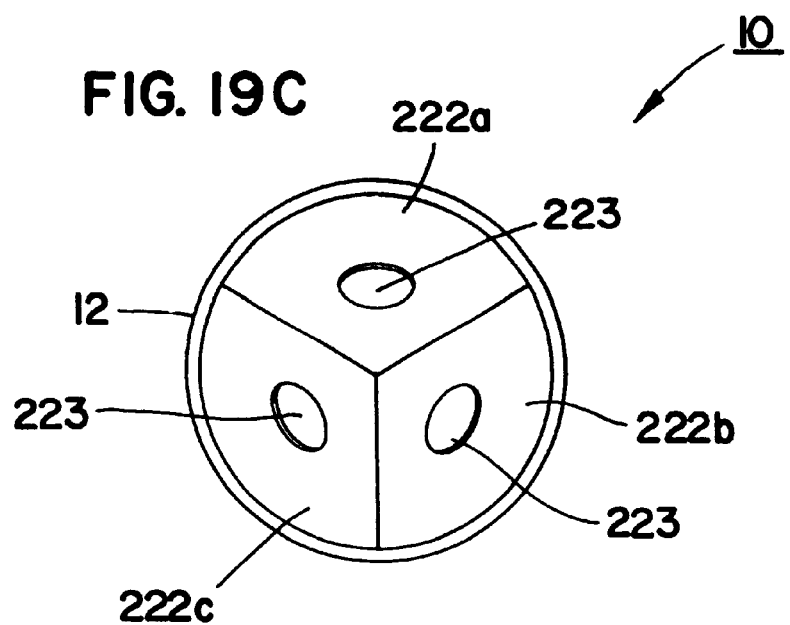
FIG. 19C is a transverse cross-sectional view of the bi-directional flow regulator of FIG. 19B.
Figure 19A:
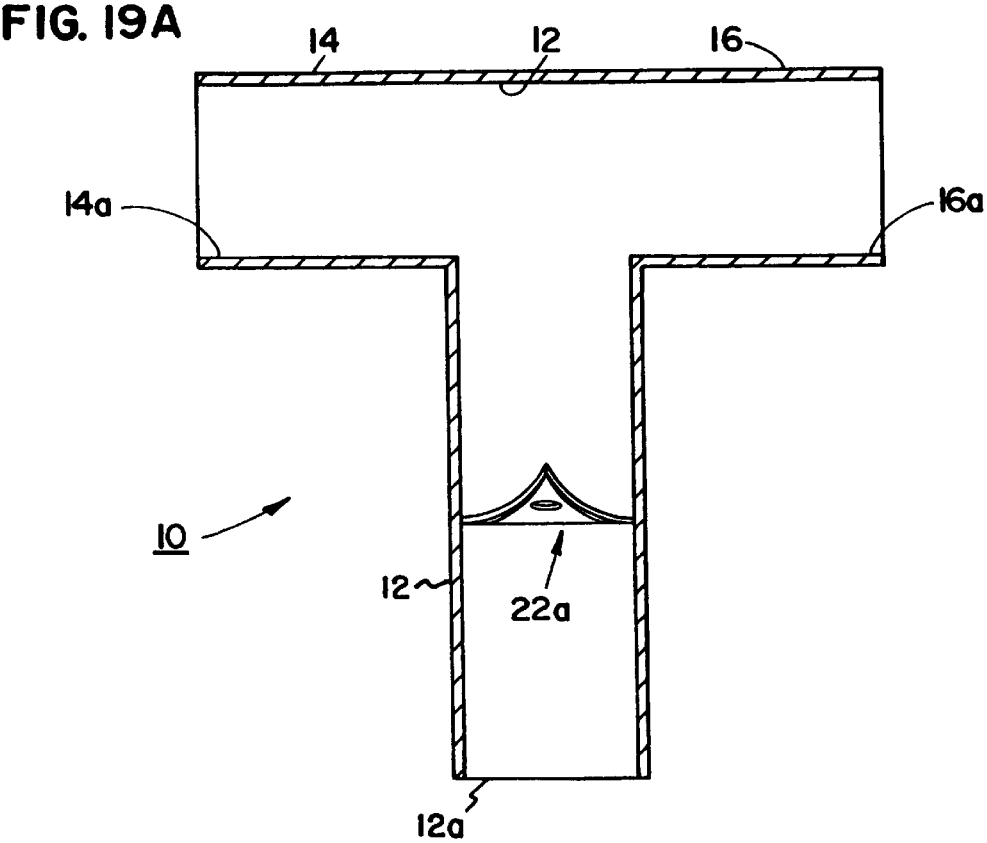
FIG. 19A is a schematic cross-section longitudinal view of an alternative embodiment of a bi-directional flow regulator shown in a full flow position.
Figure 19B:
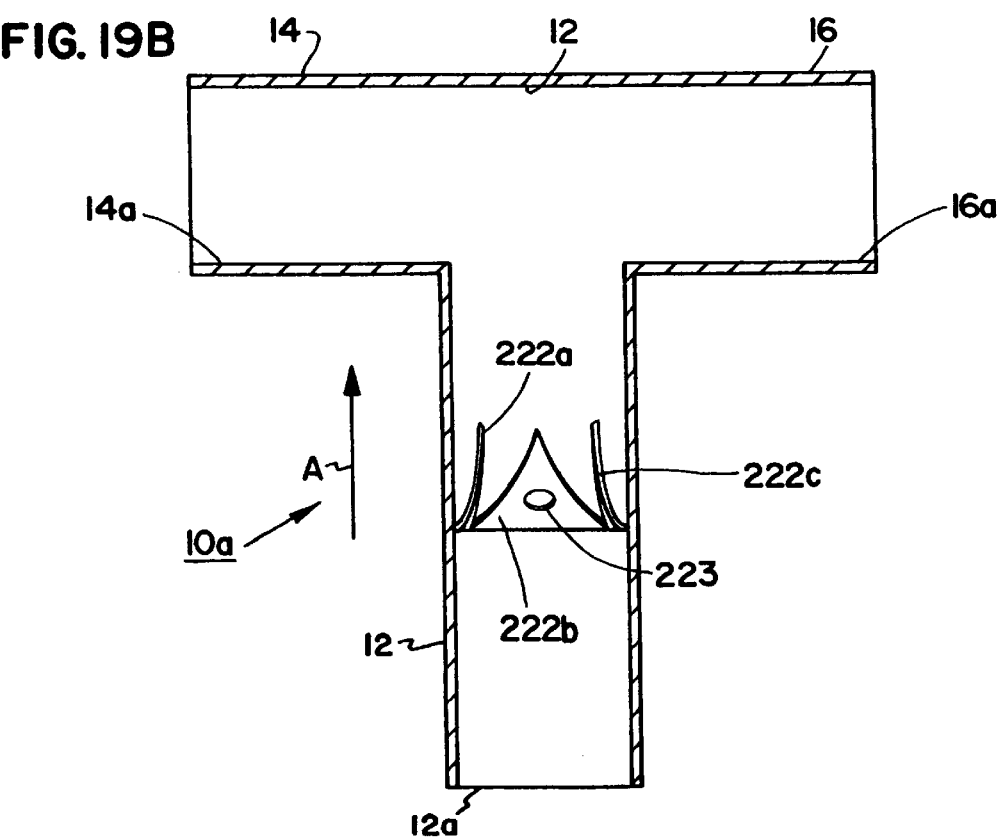
FIG. 19B is the view of FIG. 19A showing the bi-directional flow regulator in a reduced flow position.

FIGS. 18A through 18C illustrate one embodiment of a bi-directional flow regulator 22. FIGS. 19A through 19C illustrate an alternative embodiment of a bi-directional flow regulator 22. The regulator 22 of FIGS. 18A through 18C shows a butterfly valve 222 mounted in the anchor arm 12 of a rigid conduit 10. Valve 222 may be pivoted (in response to blood flow in the direction of arrow A) between a position with the plate 222 generally parallel to the walls 12 of the conduit 10 as illustrated in FIG. 18A. The plate 222 can be rotated (in response to blood flow reverse to arrow A) to a position angled relative to the walls 12 of the conduit 10 as illustrated in FIG. 18B. FIG. 18A may be conveniently referred to as a full flow position. FIG. 18B may be conveniently referred to as a reduced flow position. FIG. 18C is a cross-section of the conduit 10 when the plate 222 is in the reduced flow position.

The plate 222 is sized relative to the conduit 10 such that the cross-sectional area of the conduit 10 which remains open is sufficient to permit about 20% of the blood flow (measured volumetrically) to flow back through the conduit 10 in a direction opposite to that of arrow A during diastole. As a result, during systole, blood flow from the heart to the coronary artery urges the plate 222 to the full flow position of FIG. 18A such blood may flow unobstructed through the device to the coronary artery. During systole, the blood (due to pressure differentials between the coronary artery and the left ventricle) will flow in a direction opposite of that of arrow A causing the plate 222 to rotate to the position of FIGS. 18B and 18C. However, even in the reduced flow position, the plate 222 is prevented from moving to a full closed position such that flow through the device is never blocked and instead may proceed with a back flow of about 20% (volumetrically measured) of the normal flow in the direction of A.

FIGS. 19A through 19C show an alternative design of the conduit 10 with the flow regulator 22a in the form of three leafs 222a, 222b, 222c which, in response to blood flow from the left ventricle to the coronary artery, open to a full open position shown in FIG. 19B and move to a restricted flow position in FIGS. 19A and 19C in response to back flow. The leaves 222a, 222b, 222c are provided with openings 223 to permit flow through the leaves 222a, 222b, 222c at all times.

It is believed that providing a back flow of about 20% (20% being a non-limiting example of a presently antici-pated desired back flow rate) of the volumetric anterograde flow is necessary. This is essential because it allows the channel of the conduit 10 and the mechanical elements of the flow regulator 22 to be washed by the retrograde flow. This ensures that no areas of stagnant flow occur. Areas of stagnation, if allowed, could result in clot formation which could result in thrombi occluding the conduit or breaking loose. Thrombi could be carried downstream into the coronary arteries to cause one or more areas of cardiac muscle ischemia (i.e., a myocardial infarction) which could be fatal. Back flow necessary to wash the components can be achieved through either a conduit 10 which has a constant opening through both systole and diastole (i.e., conduit 10 of FIG. 2A without the use of a bi-directional flow regulator 22) or with a device coupled with a bi-directional flow regulator 22 (FIGS. 2B–2C) which permits a 20% flow rate back flow during diastole.

c. L-Shaped Device

Preferably, an L-shaped conduit 10' (FIGS. 1A, 1B, 1C) is used to completely bypass the coronary obstruction. An L-shaped conduit 10' has an anchor arm 12' with an open end 12a'. Unlike conduit 10, conduit 10' has only one intracoronary arm 14' perpendicular to arm 12'. Arm 14' has an open end 14a' and conduit 10' is hollow to define a continuous fluid pathway 11' from end 12a' to end 14a'. In application, arm 14' is placed within the lumen of an artery. End 14a' faces downstream from an obstruction. Arm 12' is placed through the heart wall with end 12a' in fluid communication with blood within the heart chamber. As illustrated in FIG. 1B, the anchor arm 12' can include a bi-directional flow regulator 22' similar to bi-directional flow regulator 22 of conduit 10.

d. Optional Flexible Anchor Arm

Conduit 10, 10' may be rigid, or have varying flexibilities. Regardless of such flexibility, the conduit 10, 10' should be sufficiently rigid for pathway 11, 11' to remain open during both diastole and systole. FIGS. 3A, 3B and 3C demonstrate one embodiment where the anchor arm (i.e., elements 12, 12' of FIGS. 1A and 2A) is comprised of a number of rings 17 surrounded by a membrane 18. In FIGS. 3A–3C, only anchor arm 12 is shown. It will be appreciated that anchor arm 12' may be identically constructed.

In the embodiment of FIGS. 3A–3C, the rings 17 can be constructed of Teflon, and the surrounding membrane 18 can be constructed of a double-walled Dacron sheath into which the rigid supporting rings 17 are sewn. In this embodiment, the rings 17 provide structural strength. The structural strength maintains an open lumen or conduit 11 leading into the coronary artery by preventing the conduit 11 from collapsing by reason of contraction of the heart muscle surrounding the anchor arm 12. The series of rings 17 provide a degree of flexibility which allows a channel formed through the heart chamber muscular wall (receiving anchor arm 12) to be angled or curved. In addition, the flexibility of the surrounding sheath 18 in concert with the rigid rings 17 will allow the anchor arm 12 to expand, FIG. 3B, and contract, FIG. 3C, with the contractions and relaxations of the surrounding cardiac musculature.

It should be noted that, because of the semi-rigid nature of the anchor arm 12 constructed in this manner, a method of attaching that end of the anchor arm in contact with the inner surface of a chamber of a heart can be useful. In the example illustrated, this attaching mechanism 19 is a rigid flange 12a. It will be appreciated that other mechanisms of attachment, such as suturing, biologically gluing, etc. are alternative options.

e. Optional Blood Reservoir

The apparatus of the present invention (as thus described) provides a path 11 through which blood flows from a chamber of a heart and into a coronary artery. Additionally, such a device can store blood under pressure for a period of time prior to its introduction into a coronary artery. As depicted in the embodiments of FIGS. 1C and 2D, this aspect of the conduit 10, 10' of the present invention is referred to as a capacitance pressure reservoir (CPR) 24, 24'.

Blood flow through the normal coronary artery is cyclical. Blood flow is increased during diastole (when the heart muscle is in a relaxing state), and decreases or reverses during systole (when the heart muscle is in a contracting state). See, e.g., F. Kajiya et al., *Velocity Profiles and Phasic Flow Patterns in the Non-Stenotic Human Left Anterior Descending Coronary Artery during Cardiac Surgery*, 27 CARDIOVASCULAR RES. 845–50 (1993).

The pressure gradient across the lumens 12a, 12a', 14a', 16a of the apparatus 10, 10' of the present invention will vary over the cardiac cycle. For example, during systole, the contraction of the heart muscles will generate high relative pressures within the left ventricle.

The pressures within the coronary arterioles and capillaries distal to the bypass site can also be high during this time, due to the external compression of the contracting cardiac musculature surrounding these vessels. This is particularly true for the vessels of the microcirculation deep within the heart which serve the endocardium.

The optional CPR 24, 24' stores the pressurized blood during systole for delivery to the heart muscles via the coronary circulation during diastole when pressures are reduced. In essence, the CPR 24, 24' serves a function similar to the elastic connective tissue of the thick-walled aorta. The necessary function of the CPR 24, 24' is to store blood under higher pressure, and to later provide that stored blood to the microcirculation when the external pressures on that microcirculation are reduced.

As depicted in FIGS. 1C and 2D the bi-directional flow regulators 22, 22' provide full blood flow in the direction of A, which is from a chamber of a heart into the conduit 10, 10' via the lumen 11, 11'. The pressure on the blood within the chamber of a heart will be greatest when the surrounding cardiac musculature is in the contracting phase of the cardiac cycle. Because it is during this phase of the cardiac cycle that the external pressure on the coronary artery microcirculation is also highest, blood flow through the lumen 11, 11' of the conduit 10, 10' could be limited. To counteract this tendency, the conduit 10, 10' is equipped with a reservoir 24, 24' which stores this pressurized blood flowing from a chamber of the heart during the cardiac contraction.

The reservoir, or CPR 24, 24' is schematically illustrated in FIGS. 1C, 2D. It can be appreciated that the conduit 10, 10' is provided with a fluid passage 28, 28' in communication with pathway 11, 11'. The passage 28, 28' communicates with an expandable volume (or storage chamber) 27, 27' defined by a movable wall 31, 31' contained within a fixed housing 33, 33'. Springs 29, 29' between wall 31, 31' and housing 33, 33' urge the wall 31, 31' to move to reduce the size of volume 27, 27'. The springs 29, 29' are pre-loaded to exert a force on wall 31, 31' less than a force exerted by blood within volume 27, 27' during the contraction phase of the cardiac cycle, but greater than the force exerted by blood within volume 27, 27' during the relaxation phase of the cardiac cycle.

The conduit 10, 10' is constructed in a manner which allows blood to flow into the storage chamber 27, 27' of the conduit 10, 10' through the lumen 11, 11' of arm 28, 28' of the conduit when the cardiac musculature is contracting. When blood is flowing into the storage chamber 27, 27', the kinetic energy of the flowing blood is converted to potential energy, and stored in 29, 29'. During the relaxation phase of the cardiac musculature, the potential energy stored in 29, 29' of the CPR 24, 24' is then re-converted to kinetic energy in the form of blood flow out of the storage chamber 27, 27' of the conduit 10, 10' via the lumen 11, 11' of arm 28, 28' of the conduit.

While the CPR 24, 24' is illustrated with a movable wall 31, 31' and springs 29, 29' to define a variable volume, other designs can be used. For example, the CPR 24, 24' can be a balloon-like structure. As it fills with blood, the pressure on that blood increases through the stretching of an elastic component of a balloon. In another embodiment, the CPR, 24, 24', can be a hollow bag, made of a material which is elastic, but impermeable to liquids, and pliable similar to a plastic bag. When the heart contracts, blood is forced through lumen 11, 11' of arm 28, 28' of the apparatus 10, 10' of the invention into the collection bag.

The incorporation of bi-directional flow regulators 22, 22' within the anchoring arm 12, 12' of the conduit 10, 10' provide most (about 80%) of the flow of blood out of the device during diastole to the coronary artery via the lumen 11' 11' of arms 14a, 14a', 16a of the device, of the conduit 10, 10'. Similarly, the incorporation of the bi-directional flow regulator 26 within the intracoronary arm 16 of the T-shaped conduit 10, when employed with the bi-directional flow regulator 22 within the anchor arm 20 of the conduit 10, would provide most of the flow of blood out of the device during diastole to the portion of the coronary artery distal to the bypass site via the downstream lumen 11 of arm 14a.

f. Sizing of the Conduit

The inner and outer cross-sectional diameters of a coronary artery decreases with the distance from the arterial origin. Eventually, the artery branches into a number of arterioles, which feed the capillary bed of the coronary arterial microcirculation.

The typical diameter of a lumen of a coronary artery is, in general, species specific; increasing with heart size. In humans, this lumen diameter is dependent upon which artery is being evaluated, but usually ranges from 1.0 to 4 mm in diameter, and decreases with distance from the aortic origin. In the preferred embodiment, the cross-sectional outer diameter of the intracoronary arms 14, 14', 16 of the device of the present invention should effectively approximate the diameter of the lumen of the coronary artery being bypassed, at the bypass site. This allows the complete re-approximation of the previously opened superficial wall of the coronary artery during surgical closure, without high suture or staple tension resulting. In the most preferred embodiment, the outer diameter of the intracoronary arms 14, 14', 16 of the conduit 10, 10' of the present invention is equal to the diameter of the lumen of the coronary artery which is being bypassed, at the bypass location. When a CPR is placed, the artery wall may need to be expanded by the addition of a patch, such as Dacron, well known in the art.

Also, due to smooth muscle relaxation and secondary vascular dilation, the cross-sectional diameter of a lumen of a coronary artery will increase with the oxygen demand of cardiac muscle during times of stress. The cross-sectional inner diameter of the intracoronary arms 14, 14', 16 of the conduit 10, 10' of the present invention should effectively approximate that diameter necessary to provide adequate blood flow through the downstream lumen of the conduit to effectively oxygenate the cardiac musculature normally supplied by the microcirculation of the coronary artery. In the preferred embodiment, the cross-sectional inner diameter of the intracoronary arms 14, 14', 16 of the conduit 10, 10' of the present invention should effectively approximate that diameter necessary to provide adequate blood flow through the lumen of the device to effectively oxygenate the cardiac musculature normally supplied by the microcirculation of the coronary artery during both times of cardiovascular resting and stress.

If necessary, an initial approximation of the required cross-sectional outer diameter of the intracoronary arms 14, 14', 16 of the conduit 10, 10' of the present invention can be gained by standard radiographic techniques. Also, in the alternative embodiment apparatus when a bi-directional flow regulator 22, 22' is desired, the operating pressure of the bi-directional flow regulator 22, 22' (i.e., the pressure at which the flow regulator moves from a reduced back-flow to a full forward flow position) can be determined by the dynamic measurements of coronary artery pressure, blood flow, and heart chamber pressures through selective catheterization with standard techniques. See Minoru Hongo et al., 127(3) AM. HEART J. 545–51 (March 1994).

During the coronary artery bypass procedure, the most appropriate sizing of the intracoronary arms 14, 14', 16 of the conduit 10, 10' of the present invention can be re-assessed. This can be accomplished by probing the distal and, if needed, the proximal aspects of the coronary artery at the chosen bypass site with blunt instruments of known outer diameters. Such sizing by probes is well-known in the literature. To facilitate the effective matching of the external diameter of the intracoronary arms 14, 14', 16 of the conduit 10, 10' of the present invention to the lumen 34 of the coronary artery to be bypassed, an assortment of conduits of the present invention of various diameters can be available for the surgeon to select from.

The anchor arm 12, 12' is sized to maximize net blood flow from the left ventricle to the coronary artery. Through simulation testing, a counter-intuitive indication is that maximizing the diameter of anchor arm 12, 12' is not desirable. For example, such simulation assuming diameters of 3.00 mm, 2.25 mm and 1.50 mm for an unrestricted fistula (i.e., without a flow regulator 22) suggests that the smaller diameter of 1.50 mm most closely approximates normal coronary blood flow and minimizes back flow thus maximizing net forward flow.

It is desirable that the anchor arm 12, 12' protrudes into the heart chamber such that end 12a is spaced from the heart wall. This prevents tissue growth over end 12a.

Finally, it will be noted that the anchor arm 12 defines a longitudinal axis (e.g., axis X—X in FIG. 18A). The region 15 of arms 14, 14 intersects axis X—X. The region 15 acts as a deflection surface to prevent high velocity blood flow from arm 12 impinging directly upon the coronary artery wall. Instead, the high velocity blood flow impinges upon region 15 and is directed axially into the coronary artery. As a result, the coronary artery wall covered by region 15 is protected from damage which would otherwise be caused by the high velocity blood flow and the blood components are transitioned to axial flow with a minimum of cell damaging shear.

Figure 20:
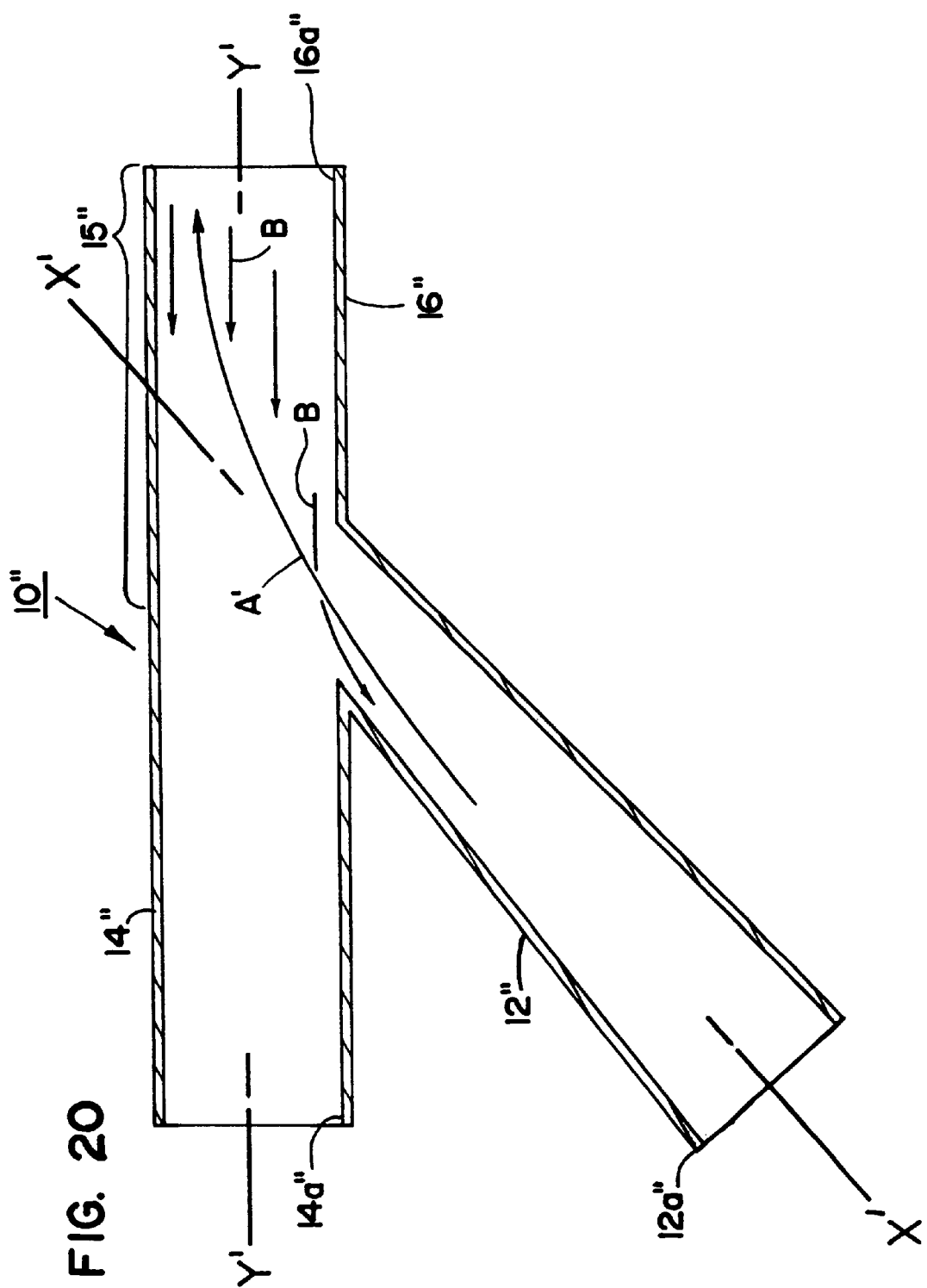
FIG. 20 is a schematic longitudinal cross-sectional view of a channel defining conduit with an alternative embodiment tapered anchor arm.

FIG. 20 shows a still further embodiment 10" where the anchor arm 12" has a longitudinal axis X'–X' at a non-orthogonal angle relative to the axis Y'–Y' of the coronary arms 14", 16". Further, the anchor arm 12" has a taper. In other words, the arm 12" is widest at opening 12a". The taper and angle act to reduce blood flow velocity and to restrict back flow (arrows B) while facilitating forward flow (arrow A'). Also, the blood in the forward flow A' impacts against the deflection region 15" at an angle to reduce impact of blood cells.

2. The Method of the Present Invention Using the Open Chest Approach a. General

The method of the present invention is suitable for performing a variety of surgical cardiac procedures. The procedures may be performed utilizing an open-chest approach, or through minimally invasive approaches by the creation of access means into the chest, or through percutaneous access utilizing intracoronary and intraventricular catheterization. Dependent on the invasiveness of the approach utilized, the heart can be allowed to pulse normally, be slowed by varying amounts, or stopped completely. A significant period of complete heart stoppage can necessitate the use of supportive cardiopulmonary bypass.

The method of the present invention for performing a coronary artery bypass procedure will now be described in detail. The patient who is to undergo the procedure can be prepared in a conventional manner for cardiac bypass surgery. The patient preparation, anesthesia utilized, and access route to the coronary circulation, will vary depending upon the invasiveness of the specific procedure chosen.

b. Preparation for the Procedure i. General Preparations

Standard techniques of general preparation for open-chest surgery in which cardiopulmonary bypass is utilized have been widely reported. See, e.g. Ludwig K. Von Segesser, Arterial Grafting For Myocardial Revascularization (1990). In one embodiment of the methods of the invention where an open-chest procedure and cardiopulmonary bypass is utilized, the patient can be prepared for surgery as outlined by Von Segesser.

General preparations for open-chest surgery in which cardiopulmonary bypass is not utilized have been published by Buffolo et al., 61 ANN. THORAC. SURG. 63–66(1996). In one embodiment of the methods of the invention where an open-chest procedure without cardiopulmonary bypass is utilized, the patient can be prepared for surgery as outlined by Buffolo.

General preparations for closed-chest surgery, to be performed using thoracoscopy and where cardiopulmonary bypass is utilized, have been outlined by Sterman et al., U.S. Pat. No. 5,452,733 (1995). In one embodiment of the methods of the invention where a closed-chest procedure and cardiopulmonary bypass is utilized, the patient can be prepared for surgery as outlined by Sterman.

General preparations for closed-chest surgery to be performed using thoracoscopy, but where cardiopulmonary bypass is not utilized, have been published by Acuff et al., 61 Ann. Thorac. Surg. 135–37 (1996). In one embodiment of the methods of the invention where a closed-chest procedure without cardiopulmonary bypass is utilized, the patient can be prepared for surgery as outlined by Acuff.

General preparations for percutaneous coronary artery bypass grafting utilizing intracoronary and intraventricular catheterization and without cardiopulmonary bypass have been described by Wilk in his afore-mentioned U.S. patents. Preparations can include the sterile scrubbing and draping of at least one groin to permit access to a femoral artery for catheterization of the coronary vasculature and the sterile scrubbing and draping of the right superior anterior chest wall to permit access to the innominate artery for catheterization of the left ventricle. Further suggested preparations can include those outlined by Sterman and Acuff for thoracoscopic surgery with and without cardiopulmonary bypass, respectively.

ii. Anesthesia Prior to and During the Procedure

Most often, the patient will be placed under general anesthesia prior to the procedure. In one embodiment, standard cardiac operative anesthetic techniques, such as premedication with diazepam, induction with propofol and sufentanil, and maintenance with desflurane can be employed. On occasion, less than general anesthesia can be utilized. Less than general anesthesia is well known in the literature. When the invasiveness of the procedure is minimal, such as when the procedure is to be carried out via intracoronary and intraventricular catheterization, or when the risks of general anesthesia to the individual patient outweighs the risks of less than general anesthesia with regard to the particular procedure planned, less than general anesthesia can be induced. Selective ventilation of the lungs can be achieved through the placement of a double-lumen endobronchial tube which independently provides for the intubation of the left and right main stem bronchi. An intraesophageal probe can be placed to facilitate cardiac monitoring and the synchronization of power to the laser, when deemed useful.

iii. Access to the Heart and Coronary Vasculature for the Procedure

Following preparation, access to the patient's coronary arterial vasculature can be attained through a variety of techniques, dependent upon the route of access chosen.

Von Segesser has reported a method of access to the coronary arterial vasculature when utilizing an open-chest approach and cardiopulmonary bypass. In one embodiment, utilizing an open-chest approach with cardiopulmonary bypass, access to the coronary vasculature can be obtained as reported by Von Segesser.

Buffolo et al. has reported an open-chest approach to the coronary arterial vasculature when performed without cardiopulmonary bypass. See Buffolo et al., 61 ANN. THORAC. SURG. 63–66 (1996). In one embodiment utilizing an open-chest approach without cardiopulmonary bypass, access to the coronary vasculature can be obtained as reported by Buffolo.

Sterman et al. has reported a method of access to the coronary arterial vasculature when a closed-chest approach with cardiopulmonary bypass is utilized. See Sterman et al., U.S. Pat. No. 5,452,733 (1995). Sterman positions a plurality of access trocar sheaths along the patient's left and right anterolateral chest wall. These trocar sheaths provide access to the coronary vasculature, and allow the temporary repositioning of the heart to facilitate the performance of the procedure. The repositioning is accomplished utilizing grasping tools introduced through the appropriate trocar sheaths. Visualization during this procedure can be either indirectly via thoracoscopy, or directly via a 'window' placed in the left middle anterior chest wall by the surgical removal of the fourth rib. Access to the bypass site can therefore be obtained by following the techniques outlined by Sterman. The instruments to be used in the procedure can also be similar to those described by Sterman.

Acuff et al. has described a method of access to the coronary arterial vasculature when a closed-chest approach without cardiopulmonary bypass is utilized. See Acuff et al., 61 ANN. THORAC. SURG. 135–37 (1996). Similar to the techniques of Sterman, Acuff positions a plurality of access trocar sheaths along the patient's left and right anterolateral chest wall. Also similar to Sterman, Acuff surgically establishes an access space, or window in the left anterior chest wall through the removal of the left fourth rib cartilage. The trocar sheaths, in concert with this window, allow the temporary repositioning of the heart, and access to the coronary arterial vasculature. Visualization during this procedure can be either indirectly via thoracoscopy, or directly via the window. Access to the bypass site can therefore be obtained by following the techniques outlined by Acuff. The instruments to be used in the procedure can also be similar to those described by Acuff.

Access to a chamber of a heart and a coronary artery when the bypass is performed through the percutaneous approach of intracoronary and intraventricular catheterization can be obtained as follows. Access to a coronary artery can be obtained by the introduction of a catheter into the left or right femoral artery through an arterial cut down procedure. The catheter can then be fed retrograde past the descending aorta, through the ascending aorta, and into the coronary artery by standard catheterization techniques. In a preferred embodiment, access to a chamber of the left side of a heart can be obtained by the introduction of a catheter into the innominate artery, also through an arterial cut down procedure. In the most preferred embodiment, access to the left ventricle is obtained by the introduction of a catheter into the innominate artery and the advancement of this catheter into the left ventricle. In this embodiment, the catheter is advanced through the ascending aorta, past the aortic valve, and into the left ventricle. Techniques by which the left ventricle is catheterized are well known in the literature. 3. Open Chest Approach In the coronary artery bypass graft procedures of the present invention, a chamber of a heart provides blood to a coronary artery. The method of the present invention can accomplish this by establishing one or more channels through the wall of a chamber of a heart which lead directly from a chamber of a heart into a coronary artery at a site distal to the narrowing or blockage. The methods of the invention in various embodiments can achieve the establishment of such a channel or channels through a variety of techniques.

Referring now to FIGS. 4, 5, 6, 7, 8, and 9, an exemplary open-chest procedure, which may or may not include cardiopulmonary bypass, by which a coronary artery bypass procedure may be accomplished will be described. The open-chest approach affords maximal access to, and visualization of, the coronary vasculature; although at the expense of injury to normal tissue.

Through the methods of the present invention, the conduit 10, 10' of the present invention, which provides blood from a chamber of a heart 43 directly into a coronary artery 30, is placed. To illustrate the invention, only placement of conduit 10' is discussed. It will be appreciated that conduit 10 can be similarly placed. In addition, examples will be limited to the embodiment of the conduit of the invention as illustrated in FIG. 1A.

Preparation for the procedure, and anesthesia prior to and during the procedure, is outlined above.

Figure 4:
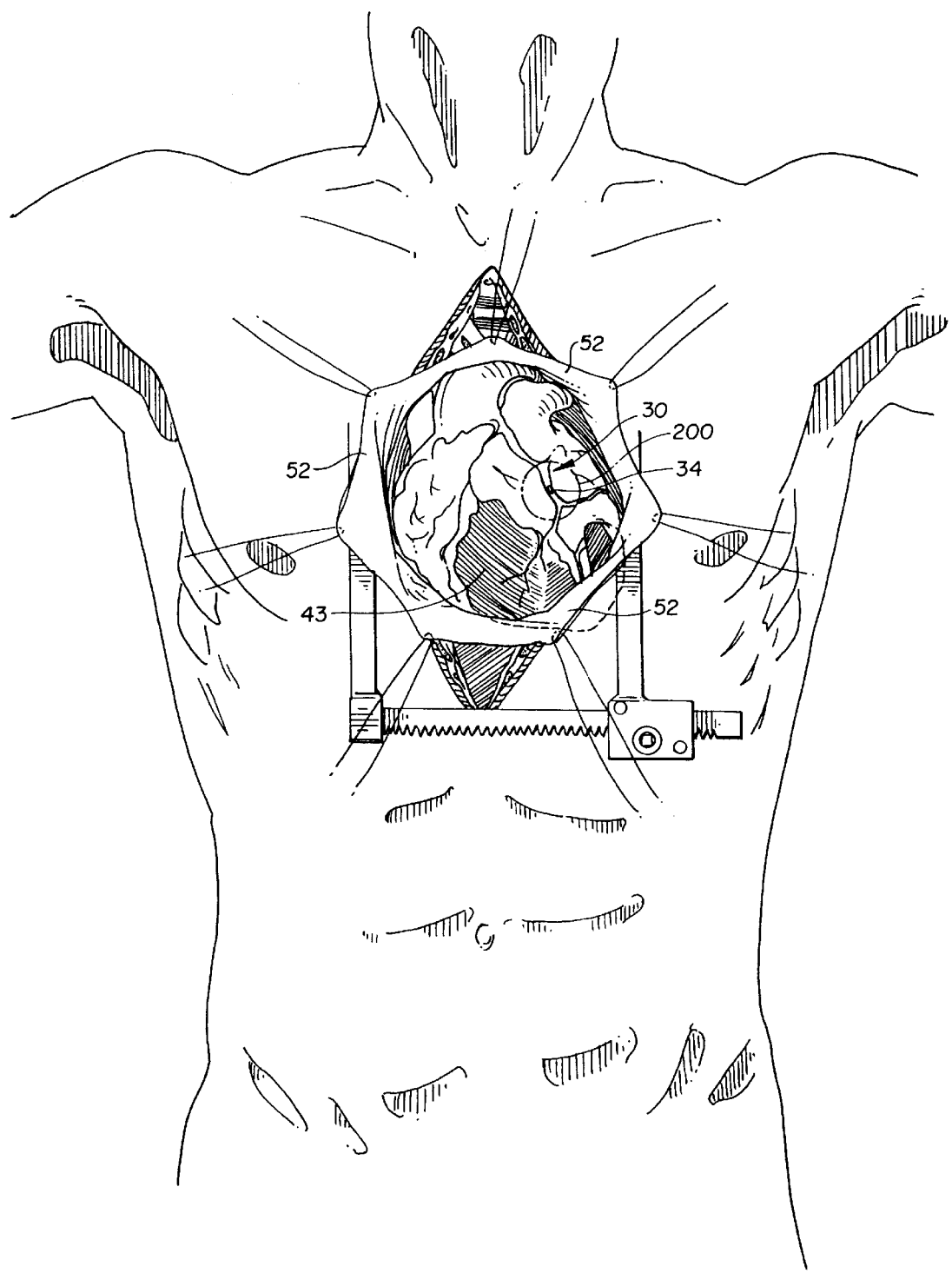
FIG. 4 is an anterior view of a human chest which is incised longitudinally to reveal a dissected pericardium and mediastinal contents.

First, the chest cavity is entered, and pericardium 52 incised anteriorly, to expose a coronary artery 30 (having an obstruction 34) to be bypassed. This is illustrated in FIG. 4.

Second, cardiopulmonary bypass may be initiated by a variety of standard techniques as outlined by George Silvay et al., *Cardiopulmonary Bypass for Adult patients: A Survey of Equipment and Techniques*, 9(4) J. CARDIOTHORAC. VASC. ANESTH. 420–24 (August 1995).

Third, if bypassed, the heart is slowed and/or stopped by a variety of standard techniques. One standard technique is to electrically induce ventricular fibrillation. Another standard technique is warm or cold blood cardioplegia, delivered antegrade or retrograde, and intermittent or continuous, as outlined by Gerald D. Buckberg, *Update on Current Techniques of Myocardial Protection,* 60 ANN. THORAC. SURG. 805–14 (1995).

Fourth, the heart is inspected and coronary arteries identified. The narrowed or occluded coronary artery 30 can be visually identified, and an appropriate site distal or downstream from the occlusion 34 chosen.

Fifth, blood flow through the target coronary artery 30 is halted by standard techniques. For example, standard techniques include clamping the aorta above the coronary ostia with an arterial clamp. Alternatively, in the beating heart procedure, the flow of blood within the coronary artery 30 can be halted by forming a loop around the artery 30 with suture either proximally, or both proximally and distally, and applying appropriate tension on the suture or sutures, or tying the suture or sutures.

Sixth, depending on the degree of exposure deemed necessary, the epicardium overlying the coronary artery at the selected bypass site is incised. This exposure can facilitate locating the lumen of the coronary artery 30 via palpation.

Figure 5:
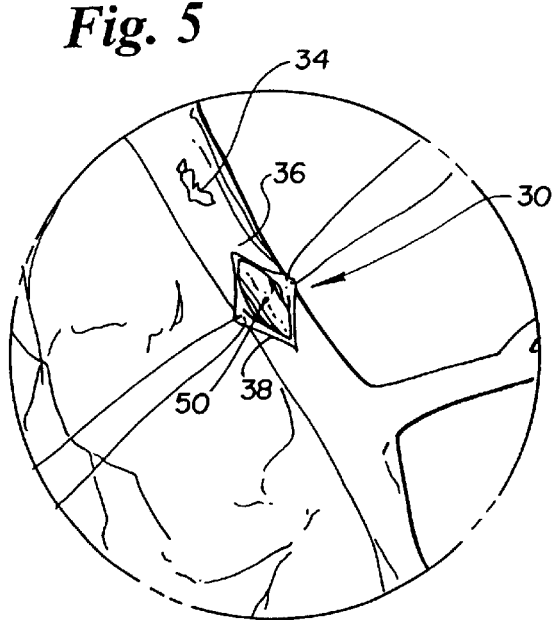
FIG. 5 is a magnified view of an area circled 200 in FIG. 4 illustrating a longitudinally incised coronary artery.
Figure 6:
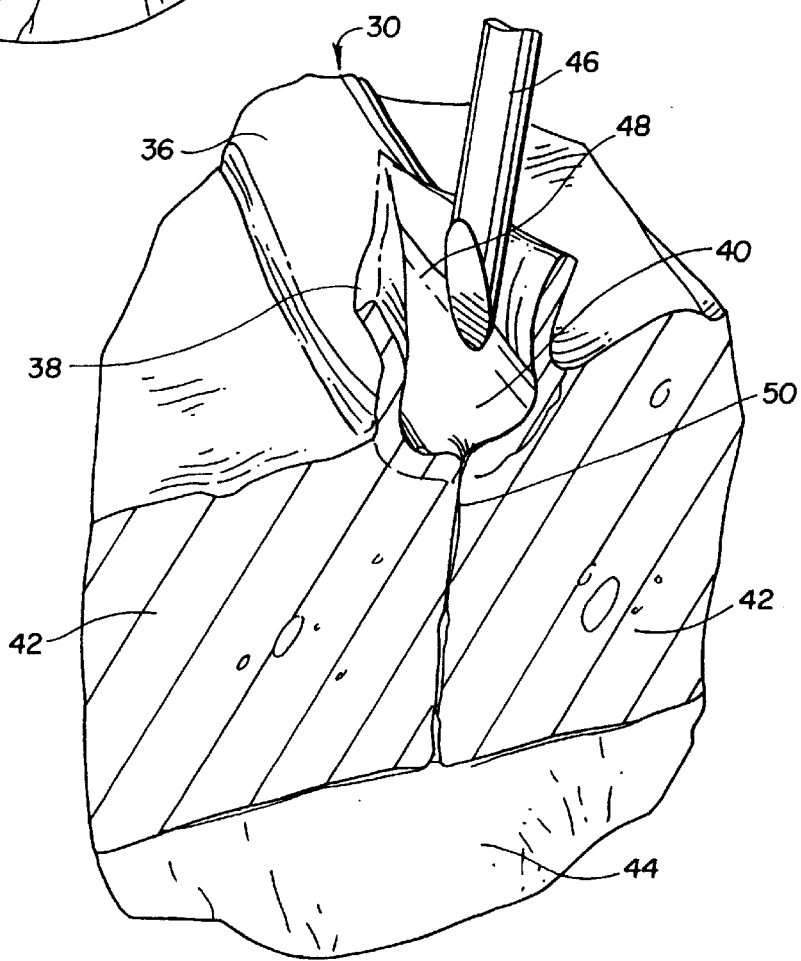
FIG. 6 is a partial external perspective view of a transversely sectioned coronary artery and heart wall illustrating a channel leading from a lumen of a coronary artery and into a chamber of the heart according to the method of the present invention.

Seventh, as shown in FIG. 5, the superficial wall 36 of the coronary artery 30 is longitudinally incised by standard techniques, such as incision with a scalpel, electrosurgical cutting device, or similar tool; taking care not to damage the deep wall of the artery. This initial incision can be lengthened, if necessary, to accommodate the intracoronary arms 14' using standard tools such as fine angled scissors.

Eighth, a channel 50 is initiated into the deep coronary arterial wall 40 and through the musculature 42 of a chamber of a heart. In the preferred embodiment, the chamber of a heart is the left ventricular chamber of the heart. The channel 50 can be initiated by standard techniques such as awl punching, incising, use of a laser, or the like. The channel 50 is then extended into the chamber of a heart, in this case the left ventricle 44, by standard techniques (such as punching with a trocar 46, incising with a scalpel blade, electrosurgical cutting with an electrosurgical cutting tool, laser or radio frequency ablation, blunt dissection, etc.).

Ninth, once a channel extending through the entire thickness of a wall 42 of a chamber of a heart is formed, it can be systematically sized by the passage of standard probes.

Tenth, through palpation, inspection, and probing of the distal and proximal coronary artery lumen 48, a conduit 10' of appropriate dimensions is selected, as outlined above.

Figure 7:
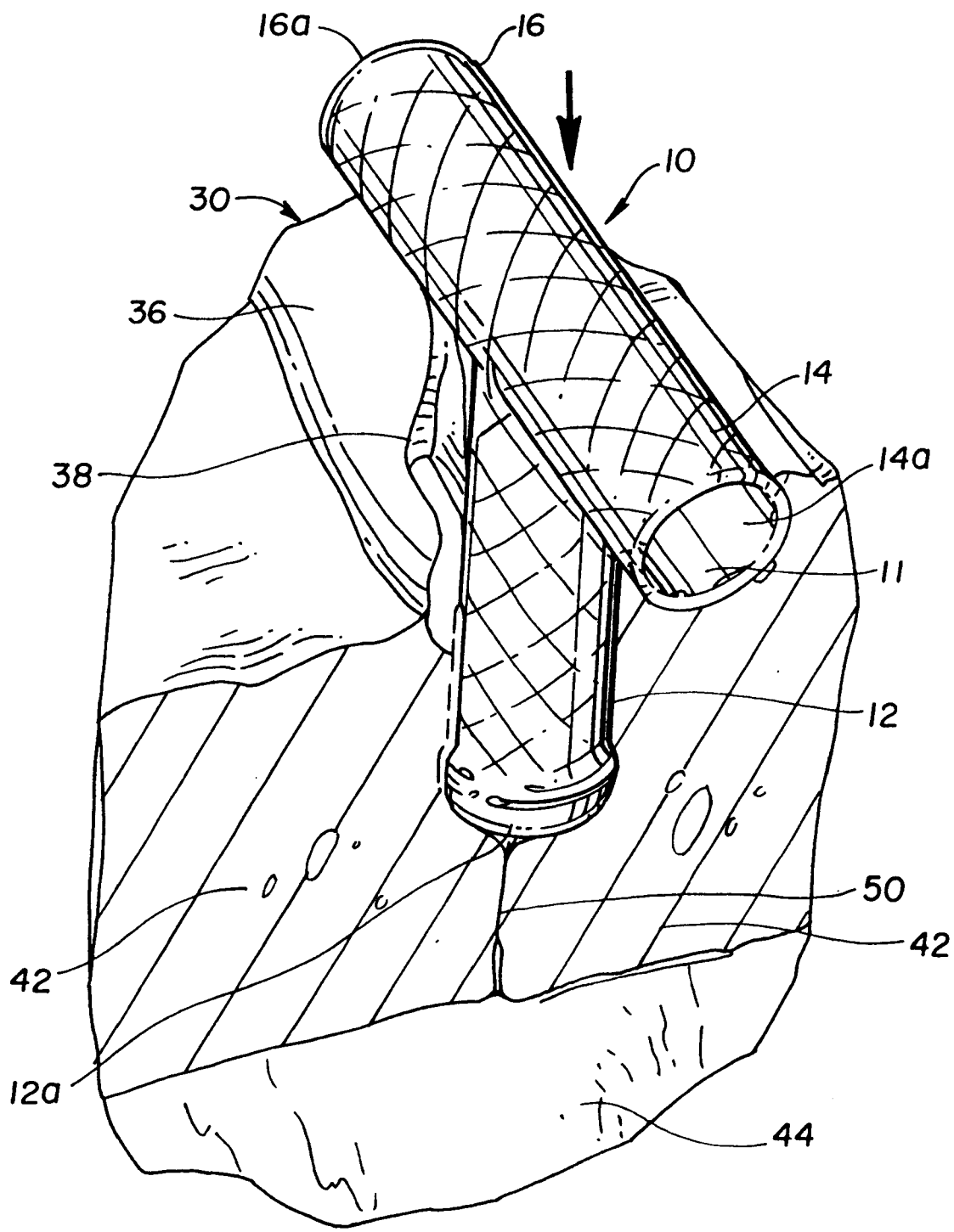
FIG. 7 is a partial external perspective view of a transversely sectioned coronary artery and heart wall illustrating the partial placement of one embodiment of the conduit of the present invention into the incised coronary artery and formed channel illustrated in FIG. 6.
Figure 8:
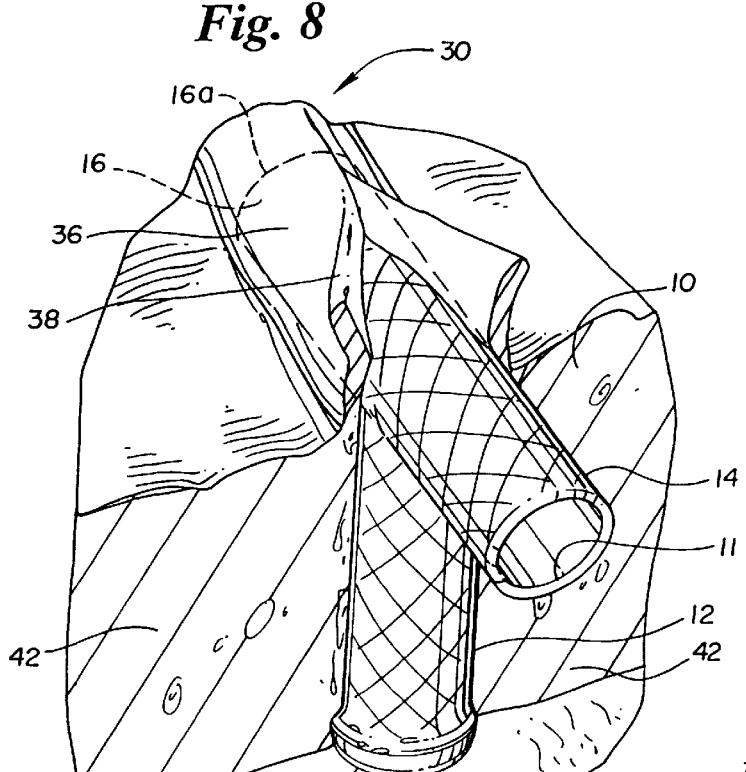
FIG. 8 is a partial external perspective view of a transversely sectioned coronary artery and heart wall illustrating the completed placement of one embodiment of the conduit of the present invention into the incised coronary artery and formed channel illustrated in FIG. 6.

Eleventh, as illustrated in FIGS. 7 and 8, the anchor arm 12' is inserted into the formed channel 50. The intracoronary arm 14' is then seated within the lumen 48 of the coronary artery 30.

Figure 9:
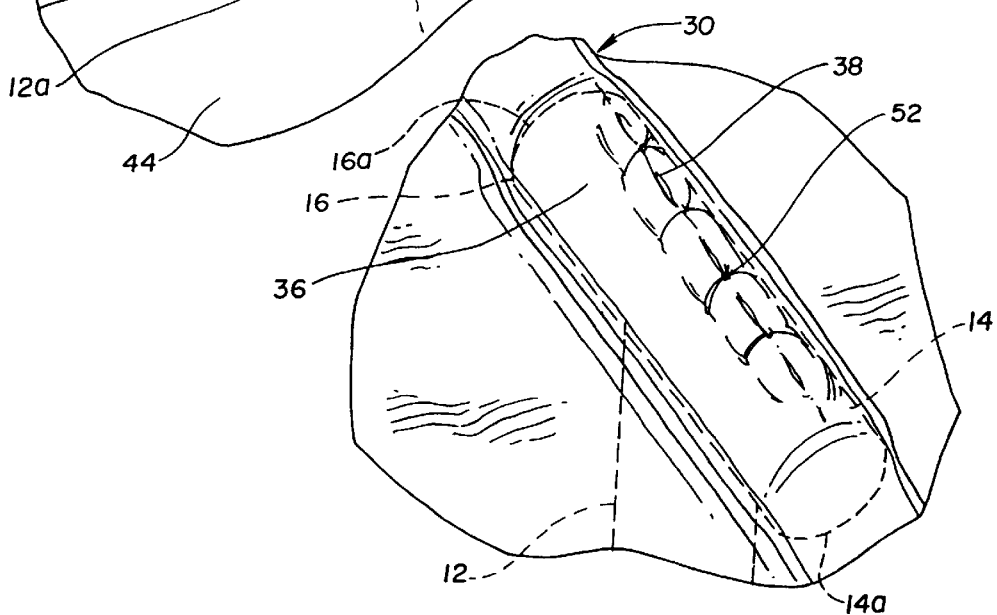
FIG. 9 is a partial external perspective view of a sutured coronary artery and phantom view of the conduit of the present invention.
Figure 10:
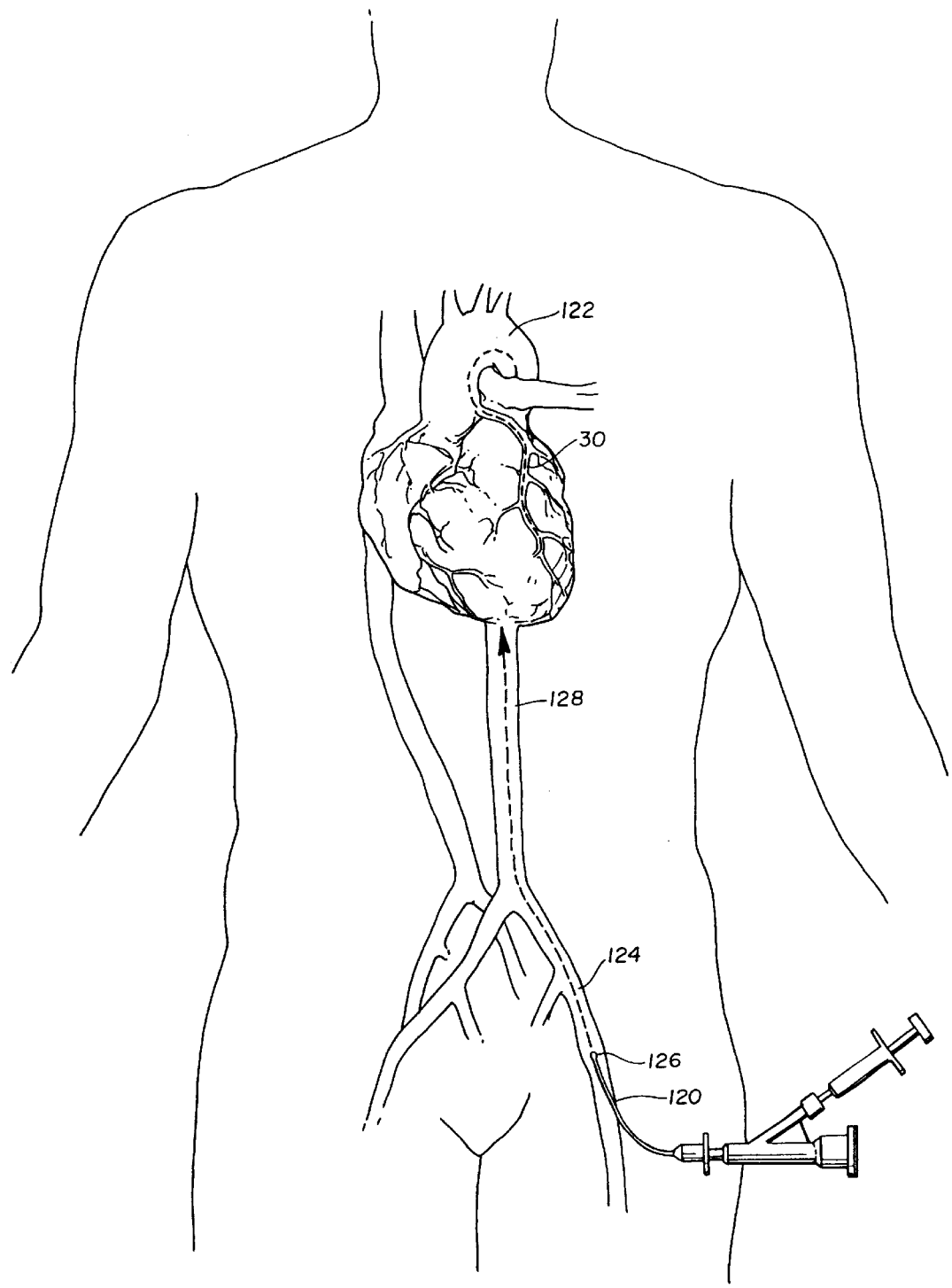
FIG. 10 is a schematic illustration of the use of an endovascular catheter to catheterize the patient's coronary artery.

Twelfth, as shown in FIG. 9, the longitudinal incision 38 previously incised in the anterior wall 36 of the coronary artery 30 is surgically re-approximated. The re-approximation can be performed by a number of conventional techniques, including suturing 52, laser welding, microstapling, and the like.

Thirteenth, the clamps or sutures closing off blood flow to the coronary artery are released.

Fourteenth, contractions of the heart, if previously stopped, are reinitiated by standard electrostimulation or the reversal of cardioplegia and the patient is slowly weaned from cardiopulmonary bypass by standard techniques.

Fifteenth, the pericardium, sternum, and overlying skin of the chest is re-approximated and surgically closed by standard, conventional techniques.

Sixteenth, anesthesia is reversed and the patient revived by standard techniques.

D. Embodiments for a Closed Chest Approach

1. The Apparatus of the Present Invention for Use in the Closed Chest Approach

A closed chest approach according to the method of the present invention may use the conduit 10, 10' as described above. Such a procedure will now be described. Following this description, a closed chest approach using alternative embodiments of the apparatus of the invention will be described.

2. The Method of the Present Invention Using the Closed Chest Approach

An exemplary closed-chest procedure, without cardiopulmonary bypass, by which a coronary artery bypass may be accomplished will now be described. The closed-chest approach is less invasive than the open-chest approach, although providing the surgeon with somewhat poorer visualization and limited direct access to both the chambers of the heart and coronary artery bypass site.

Preparation for the procedure, and anesthesia prior to and during the procedure, is outlined above.

First, a plurality of access trocar sheaths is positioned anterior and laterally along the left and right chest walls as outlined by Acuff et al.

Second, a space in the left low anterior chest wall may be formed by removal of the fourth rib cartilage, as outlined by Acuff et al. In this embodiment, the heart and coronary artery can be both directly viewed via this space or window, as well as indirectly visualized via a thoracoscope.

Third, a standard pericardiotomy is performed using a scalpel or electrosurgical cutting tool introduced through the left lateral chest trocar sheaths while viewing under thoraocoscopy. The pericardium can be excised and either spread open, or removed from the thoracic cavity as outlined by Acuff et al.

Fourth, if necessary, the heart can be rotated within the mediastinum. Direct access and visualization through the formed chest wall space can require rotation of the heart. Rotation of the heart can be accomplished by the grasping of the heart by tools inserted through access trocar sheaths located along the left and right chest wall as described by Sterman et al. Alternatively, traction on sutures placed in the pericardium can distract the heart allowing appropriate direct visualization of the area to be bypassed as described by Acuff et al. In another alternative procedure, the heart can be accessed from the patient's back with an endoscope for implantation of the stent in the posterior vascular beds which are not currently accessible by minimally invasive techniques.

Fifth, once the coronary artery to be bypassed is identified and well-visualized; snare sutures of 5–0 polypropylene are placed at least proximally to the target area as described by Acuff et al.

Sixth, the heart rate can be pharmacologically slowed to approximately 40 beats/minute to minimize motion within the operative field as described by Acuff et. al. Nitroglycerin and heparin can also be administered to reduce cardiac ischemia and prevent clotting respectively as outlined by Acuff et al.

Because cardiopulmonary bypass is omitted in this embodiment, intermittent coronary artery occlusion to induce ischemic preconditioning, as well as transesophageal echocardiography to review cardiac wall motion changes, can be utilized as described by Acuff et al. The epicardium can be incised over the area selected for bypass and the anterior surface of the artery cleared under direct visualization through the space or window, or via remote instruments inserted through the trocar sheaths under thoracoscopic guidance.

Seventh, in situations where the coronary artery can be directly viewed, the lumen 48 of the coronary artery is identified by palpation. Either under direct visualization, or under thoracoscopic guidance and using instruments manipulated through the trocar sheaths, the superficial wall 36 of the coronary artery is then longitudinally opened. As above, care is taken to leave the deep wall 40 of the artery undamaged. The incision 38 can be enlarged, as necessary, to accommodate the intracoronary arms 14, 14', 16 of the conduit 10, 10' using fine angled scissors. This enlargement can be performed with standard surgical scissors under direct viewing through the window, or via other surgical instruments remotely manipulated following their insertion through the trocar sheaths.

Eighth, a channel 50 through the heart wall is initiated by incising or laser ablating into the deep wall 40 of the coronary artery. This also can be performed by standard surgical tools under direct viewing, or by the remote manipulation of specialized instruments introduced through the trocar sheaths and viewed thoracoscopically. The channel 50 is then extended through the deep coronary arterial wall 40, through underlying cardiac musculature 42, and into the underlying chamber of the heart 44 by incising with a scalpel or electrosurgical cutting blade, laser ablation, blunt dissection, or the like. In the preferred embodiment, a chamber of a heart 44 is one of the two chambers of the left side of the heart. In the most preferred embodiment, a chamber of a heart 44 is the left ventricle.

Ninth, the channel 50 extending through the entire thickness of a muscular wall 42 can be systematically sized by the passage of standard measuring probes. These standard measuring probes, with fixed and known tip diameters, can be similarly used to size and determine the proximal and distal patency of the coronary artery being bypassed.

Tenth, through direct and/or thoracoscopic inspection of the coronary artery lumen 48, or by probing as outlined above, an appropriately dimensioned conduit 10, 10' of the present invention is selected. As in the case of the open-chest approach (outlined above), an array of conduits 10, 10' of various sizes can be available for the operation.

Eleventh, either under direct control and visualization, or by indirect manipulation and thoracoscopic viewing, the anchoring arm 12, 12' of the conduit 10, 10' of the invention is inserted into the formed channel 50. By similar techniques the remaining intracoronary arm or arms 14, 14', 16 of the conduit 10, 10' are seated within the lumen 48 of the coronary artery 30 being bypassed. In one embodiment where the procedure is performed under thoracoscopic viewing, the conduit 10, 10' can be introduced into the cardiac cavity through the space or window previously formed within the anterior inferior aspect of the left chest wall. In this embodiment, the conduit 10, 10' can be grasped, once introduced into the chest cavity, by surgical instruments inserted through the trocar sheaths and remotely manipulated into position. In this manner the anchor arm 12, 12' of the conduit 10, 10' is then inserted into the channel formed 50 via the remote manipulation of these instruments.

Twelfth, the incision present in the superficial wall 38 of the coronary artery 30 is closed by conventional surgical techniques such as suturing, laser welding, microstapling, and the like. When closure is by indirect thoracoscopic versus direct viewing, suturing, laser welding, microstapling and the like can be accomplished by utilizing surgical instruments remotely manipulated following their introduction through the trocar sheaths.

Thirteenth, upon completion of placement of the conduit 10, 10' of the present invention, the heart, if rotated, can be returned to its normal orientation.

Fourteenth, all heart manipulating devices are removed from the chest cavity.

Fifteenth, contractions of the heart can be allowed to return to their normal resting rate by the discontinuation of intravenous esmolol and diltiazem, if utilized.

Sixteenth, the pericardium 52 is partially or completely re-approximated. An external drain can be placed inside the pericardium, as needed, as described by Acuff et al.

Seventeenth, the trocar sheaths are removed, and all thoracic punctures surgically repaired in a conventional manner.

Eighteenth, anesthesia is reversed and the patient revived by standard techniques.

E. Embodiments with the Catheter-controlled Approach

Referring now to FIGS. 10, 11, 12, 13, 14, 15, and 16, an exemplary coronary artery bypass procedure performed through catheterization will be described. This approach allows no direct visualization of the coronary vasculature, although the chamber of the heart could be indirectly visualized during the procedure by equipping the intraventricular catheter with a standard fiber-optic device, if desired. Because the procedure is performed through catheters introduced remotely, normal tissue injury is minimized.

Preparation for the procedure, and anesthesia prior to and during the procedure, is outlined above.

In the embodiment to be described, cardiopulmonary bypass is unnecessary. However, the procedure would be in no way limited if cardiopulmonary bypass were performed.

First, an intracoronary catheter 120 (FIG. 10) is inserted via an incision in the groin 126 and advanced within the femoral artery 124. Through continued advancement within the descending aorta 128, and the ascending aorta 122, the coronary artery 30 is entered.

Dependent on the degree of narrowing or occlusion of the coronary artery, standard angioplasty, atherectomy, or some similar procedure can be optionally performed if passage of the catheter tip 136 (FIG. 11A) is hindered. Angioplasty, arthrectomy, and the like could optionally precede the catheter-controlled bypass procedure.

If desired, the heart may be slowed while catheterizing the coronary vasculature, during the construction of a channel or channels 50 leading from a chamber of a heart 44 into a lumen of a coronary artery 30 itself, or both. Such slowing can improve visualization of the catheters as facilitated by fluoroscopy or the alternative radiologic techniques by which the procedure can be performed. Standard pharmacologic methods, as described above, to slow the heart are well known in the literature.

Second, the intracoronary catheter 120 is advanced within the coronary arterial vasculature tree to the target location through standard catheter manipulation techniques. The proper location of the intracoronary catheter tip 136 in relation to the targeted bypass site can be determined through standard radiographic techniques.

Figure 11A:
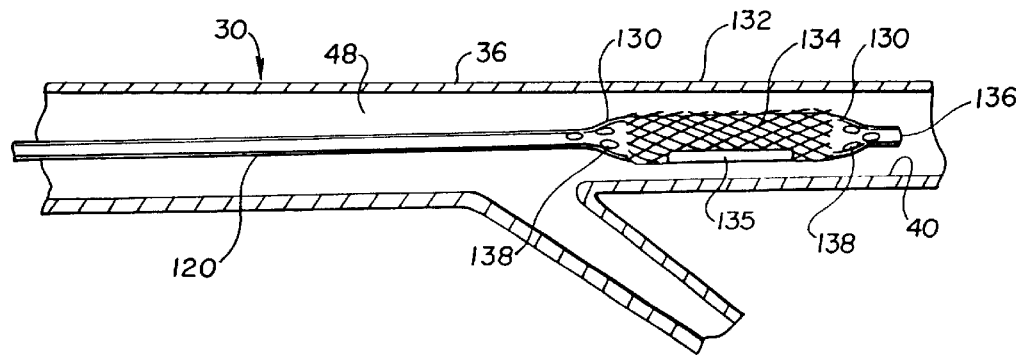
FIG. 11A is a cutaway side elevation view of the coronary artery of the bypass procedure illustrating an intravascular catheter with distally-located stent prior to inflation of a catheter balloon underlying the stent.
Figure 11B:
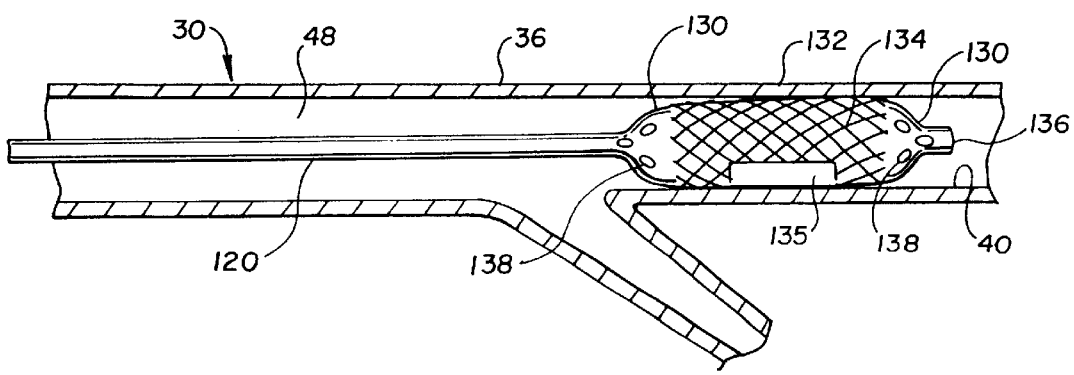
FIG. 11B is a cutaway side elevation view of the coronary artery of the bypass procedure illustrating the intravascular catheter with distally-located stent following inflation of the catheter balloon underlying the stent.
Figure 11C:
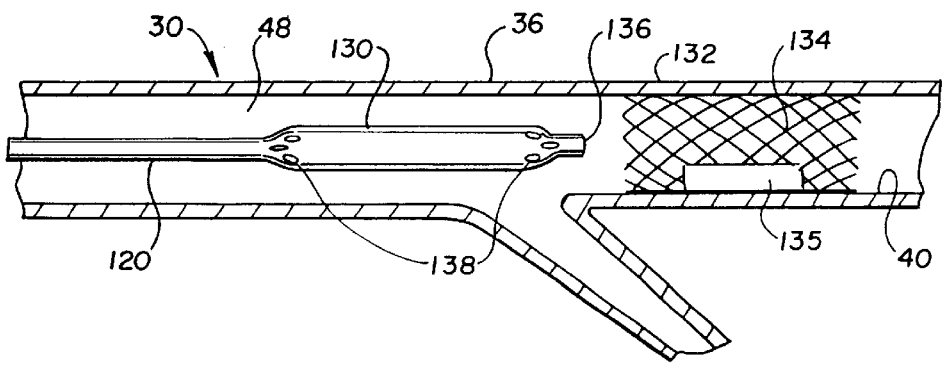
FIG. 11C is a cutaway side elevation view of a coronary artery illustrating the stent seated to the walls of the coronary artery and the catheter partially withdrawn following deflation of the catheter balloon.
Figure 13A:
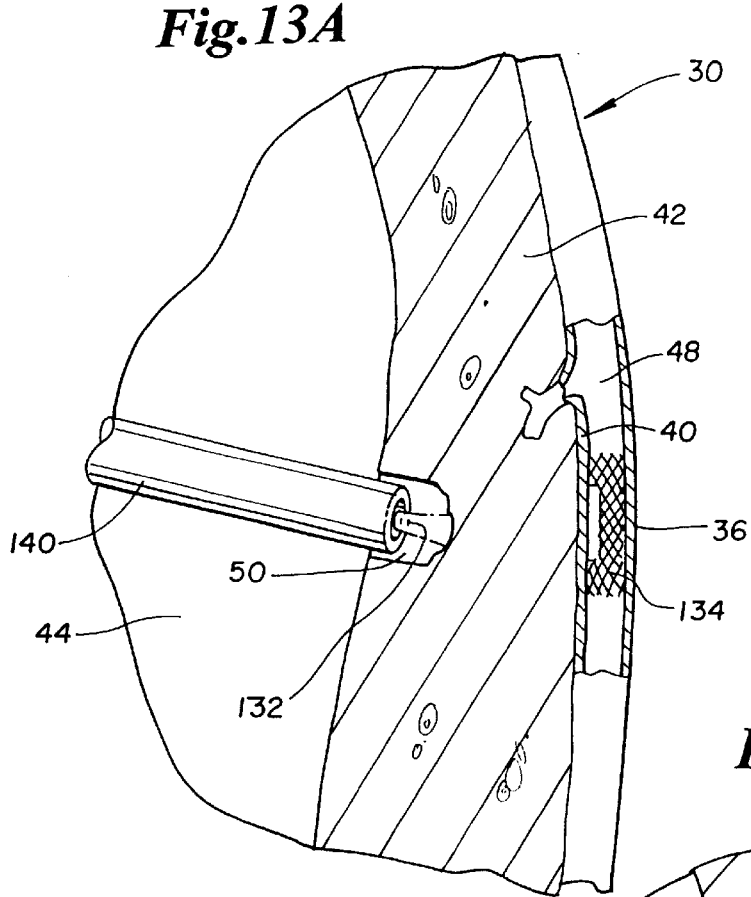
FIG. 13A is a cutaway view of the left ventricle and a partial cutaway view of the coronary artery with seated stent illustrating the formation of a channel into the wall of the left ventricle.
Figure 13B:
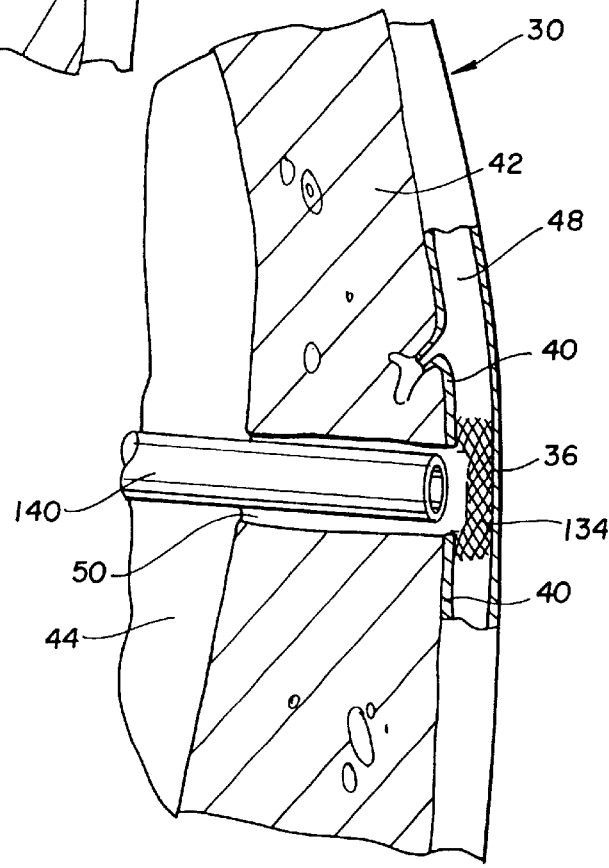
FIG. 13B is a cutaway view of the left ventricle and a partial cutaway view of the coronary artery with seated stent illustrating a completed channel through the wall of the left ventricle and deep wall of the coronary artery at the chosen bypass site.

Third, as shown in FIGS. 11A–11C, a balloon 130 located on the distal end of the intracoronary catheter 120 is inflated (FIG. 11B). Inflation of the balloon 130 causes a stent 134 located circumferentially surrounding the balloon 130 to be seated against the coronary arterial walls 36, 40. The stent 134 is a hollow expandable stent having a cut-out area 135 along the cylindrical wall of the stent 134, for reasons that will become apparent. The stent 134 is positioned at placement within the coronary artery in a manner that the cut-out 135 is juxtaposed against the deep wall 40 of the coronary artery 30 upon inflation of the intracoronary catheter balloon 130.

Fourth, the balloon 130 is deflated (FIG. 11C) and the catheter 120 withdrawn into the ascending aorta 122 leaving the expanded stent 134 in place.

Fifth, an intraventricular catheter 140 is inserted into the innominate artery 144 via an incision in the anterior superior right chest wall 142 as shown in FIG. 12. The intraventricular catheter 140 is advanced in a retrograde fashion through the ascending aorta 22, and into the chambers of the left side of the heart. By continued advancement, the intraventricular catheter 140 is extended past the semilunar valves 148 and into the left ventricle 44. Throughout the procedure, the location of the intraventricular catheter 140 within a chamber of a heart 44 can be ascertained by either indirect visualization employing standard fiber-optic instrumentation inherent to the intraventricular catheter, or and/or by standard radiographic techniques.

Sixth, a channel 50 can be ablated (FIGS. 13A–13B) through both a wall of a chamber of a heart 42 and the deep wall of a coronary artery 40 utilizing an ablating tip 132. Such ablating devices are well known in the literature and can include a laser, a radio frequency device, or the like. Power to the ablating tip 132 can be synchronized via the intraesophageal probe such that ablation occurs at a recurring aspect of the cardiac cycle. Such synchronization of devices to physiological function is well-known in the literature. The ablation can be indirectly observed via fiber optics associated with the intraventricular catheter 140. Alternatively, the location of the ablating tip 132 can be determined by standard radiographic techniques.

Seventh, once a channel 50 through the heart chamber wall 42 is formed, the intracoronary catheter 120 is re-advanced into the coronary artery 30.

Figure 14A:
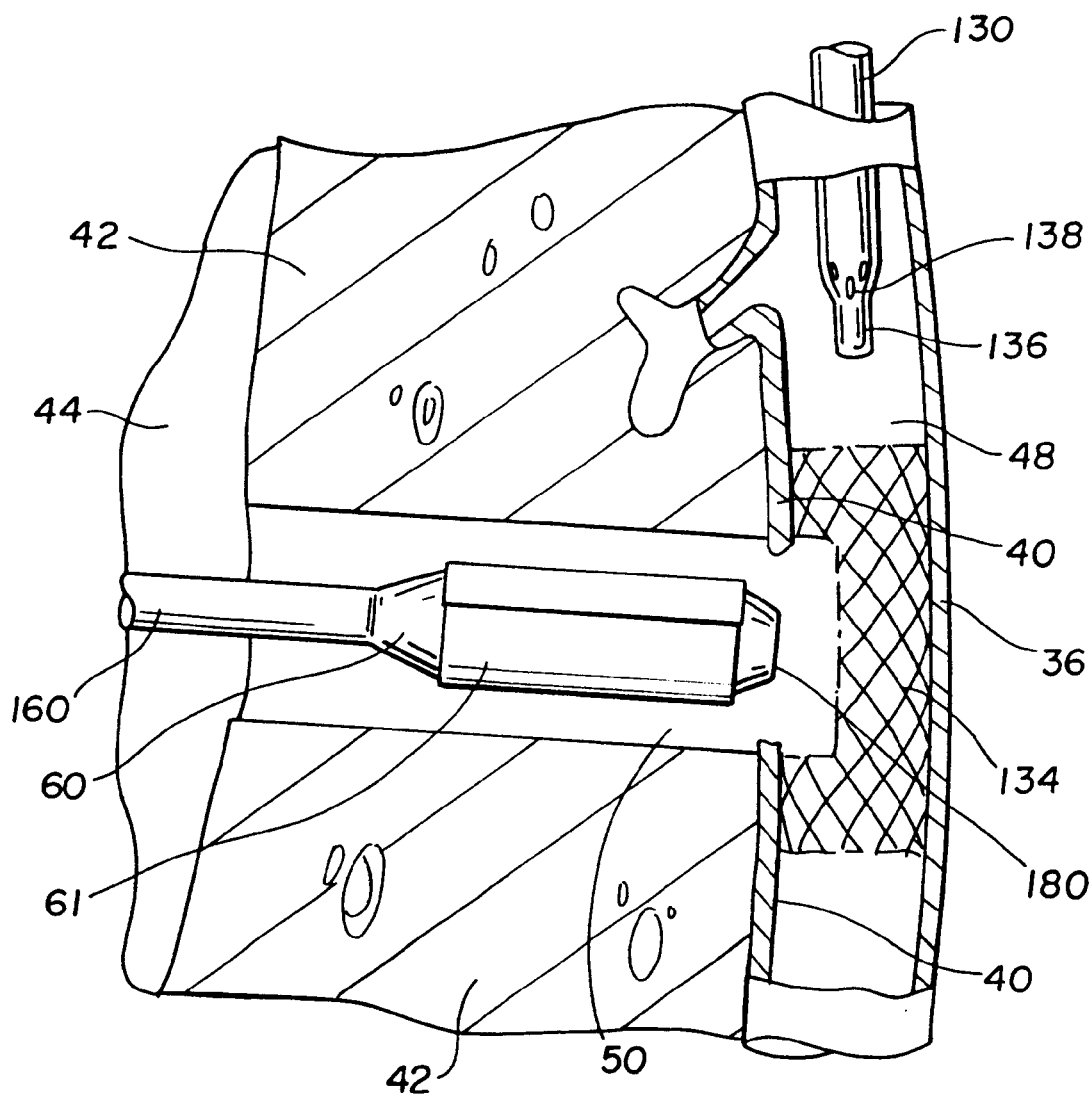
FIG. 14A is a cross-sectioned view of the left ventricle and a partial cutaway view of the coronary artery with seated stent illustrating the placement of the second intraventricular catheter within the formed channel.
Figure 14B:
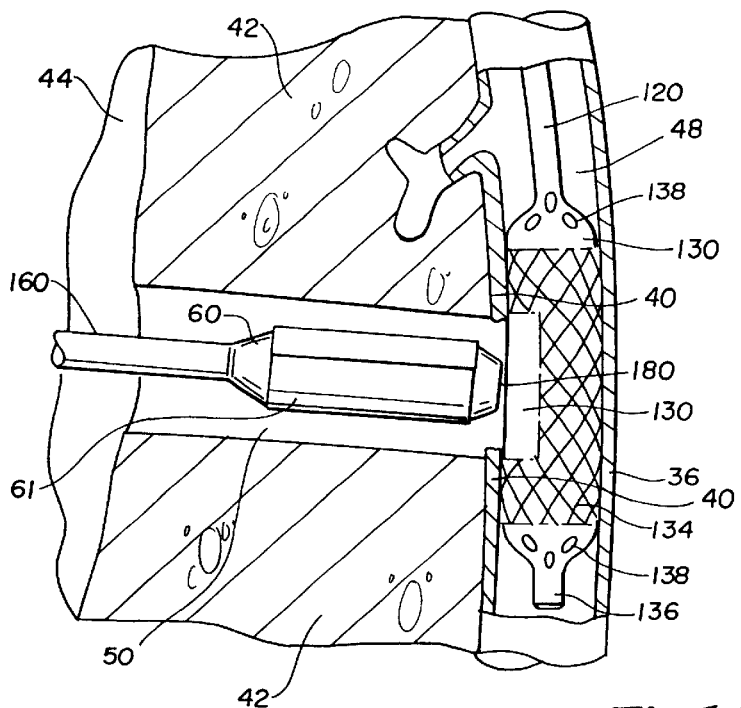
FIG. 14B is a cross-sectioned view of the left ventricle and a partial cutaway view of the coronary artery with seated stent illustrating a blockage of the formed channel by the re-inflated balloon of the intracoronary catheter.

Eighth, the balloon 130 on the distal end of the intracoronary catheter 120 is re-inflated upon reaching the target bypass site, as illustrated in FIGS. 14A and 14B. Inflation of the intracoronary catheter balloon 130 seals the formed channel 50 so that blood is prevented from flowing from the coronary artery lumen 48, through the formed channel 50, and into a chamber of the heart 44. Note, though, that the inflation of the intracoronary catheter balloon 130 still allows blood to perfuse the downstream portion of the coronary artery 30. This is because the intracoronary catheter 120 is equipped with channels 138 which allow blood to pass internally within the intracoronary catheter 120 from the upstream portion of the coronary artery 30, and to exit the catheter into the downstream portion of the coronary artery 30.

Ninth, the ablating catheter 140 is removed from the body completely.

Tenth, a second intraventricular catheter 160 is inserted into the innominate artery 144 at the arterial cut-down site 142, as shown in FIG. 12. The intraventricular catheter 160 is next advanced in a retrograde fashion into the ascending aorta 22. By continued advancement, the intraventricular catheter 160 is finally extended past the semilunar valves 148 and into the left ventricle 44.

This intraventricular catheter is equipped with a inflatable balloon 60 on the catheter's distal end, and a stent-forming device 61 circumferentially surrounding the balloon 60 on the catheter's distal end (FIGS. 14A–14D).

Figure 15A:
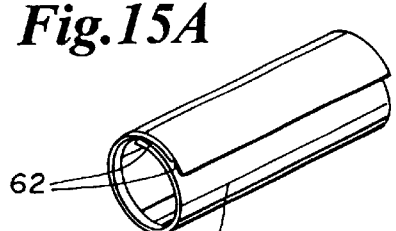
FIG. 15A is a right anterior superior perspective view of the device placed within the formed channel in its spiral shape.
Figure 15B:
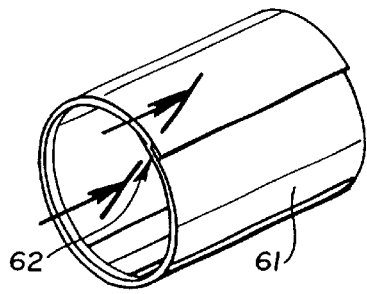
FIG. 15B is a right anterior superior perspective view of the device placed within the formed channel in its cylindrical form.

The stent forming device 61 is a spiral sheet shown separately in FIGS. 15A and 15B. Initially, the device 61 is a sheet formed in a spiral shape as shown in FIG. 15A to present a reduced diameter smaller than the diameter of the formed channel 50. In response to expanding forces (e.g., expansion of a balloon 60 within device 61), device 61 expands to a cylinder as shown in FIG. 15B. Interlocking tabs 61a and recesses 61b on opposing edges of the device 61 define a locking mechanism 62 to retain the device 61 in a cylindrical shape. The cylindrical shape of device 61 after expansion of the balloon 60, as shown in FIG. 15B, is larger in diameter than the spiral shape of device 61 prior to expansion of the balloon 60, as shown in FIG. 15A. The device 61 as expanded is sized to be retained within the formed channel 50 upon expansion.

Throughout this portion of the procedure, the location of this second intraventricular catheter 160 within a chamber of a heart 44 can be ascertained by either indirect visualization employing standard fiber-optic instrumentation inherent to the second intraventricular catheter, or and/or by standard radiographic techniques.

Eleventh, the tip 180 (FIG. 14A) of the second intraventricular catheter 160 is introduced into and advanced within the formed channel 50.

Figure 14C:
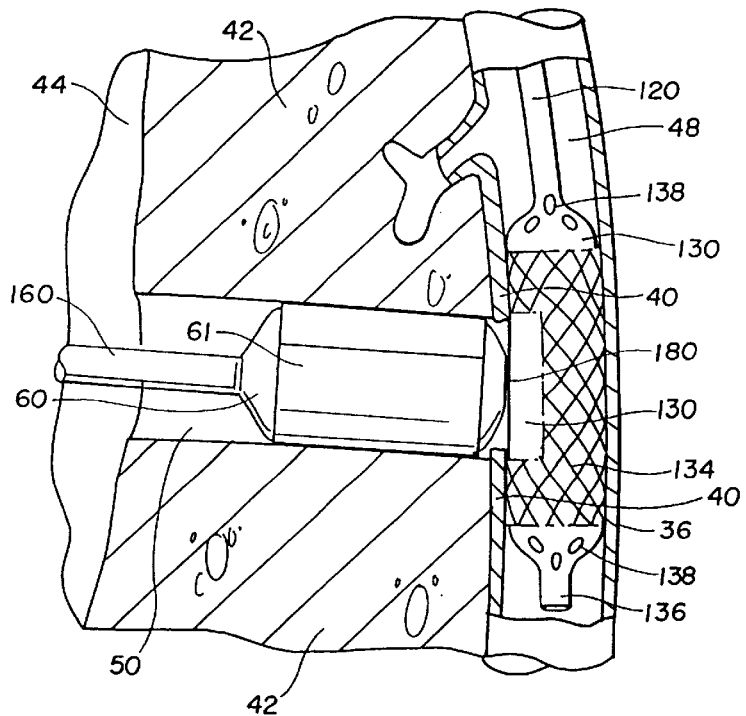
FIG. 14C is a cross-sectioned view of the left ventricle and a partial cutaway view of the coronary artery with seated stent illustrating an inflation of the balloon located on the distal end of the intraventricular catheter and the seating of an overlying spiral-shaped device against the walls of the formed channel.
Figure 14D:
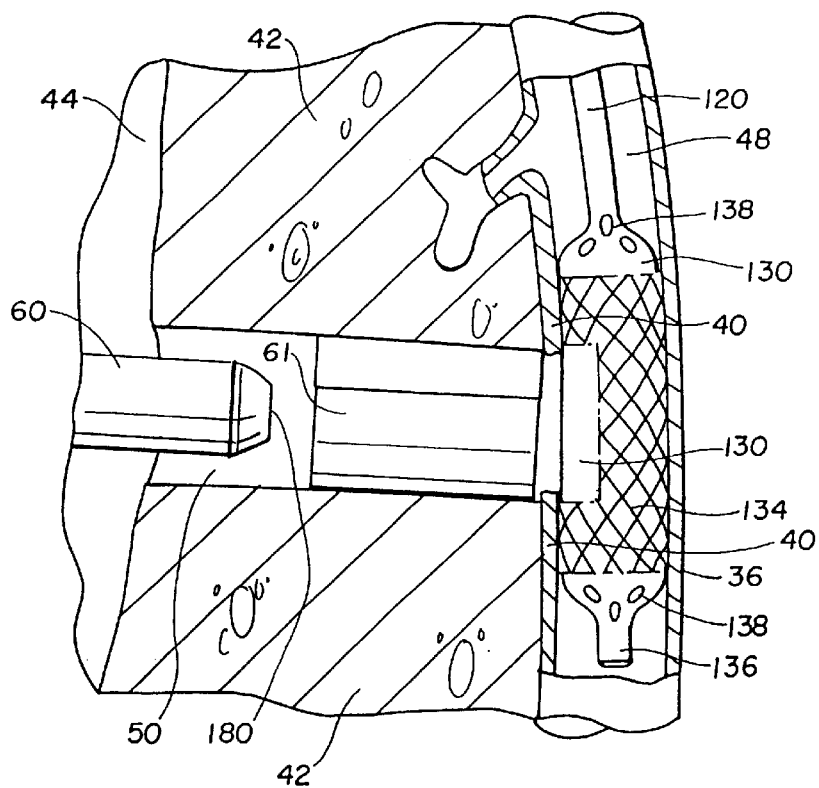
FIG. 14D is a cross-sectioned view of the left ventricle and a partial cutaway view of the coronary artery with seated stent illustrating the device in its locked cylindrical shape seated against the channel walls and the partially withdrawn second intraventricular catheter.

Twelfth, with the tip 180 of the second intraventricular catheter 160 near or abutting the side of the intracoronary catheter balloon 130, a balloon 60 surrounding circumferentially the tip of the second intraventricular catheter 160, is inflated. As shown in FIGS. 14C and 14D, inflation of the balloon 60 causes the device 61 located circumferentially around the balloon 60 located on the end of the second intraventricular catheter 160 to become seated against the walls of the formed channel 50.

Figure 16:
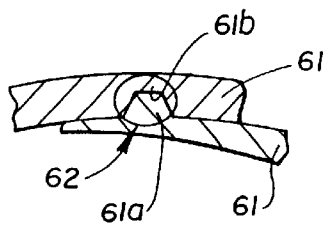
FIG. 16 is a cross-sectional view of an interlocking mechanism of the device of FIGS. 15A and 15B in its locked position.

As shown in FIG. 16, the device 61, is locked into the cylindrical position when the underlying balloon 60 is inflated by an interlocking mechanism 62 constructed as part of the device 61.

Thirteenth, the balloon 60 on the intraventricular catheter tip is deflated, and the catheter removed from the body, as shown in FIG. 14D.

Fourteenth, a third intraventricular catheter 70 is inserted at the innominate artery access site 142. This third intraventricular catheter 70 is then advanced in a retrograde fashion into a chamber of the left side of a heart, as outlined above.

Figure 17A:
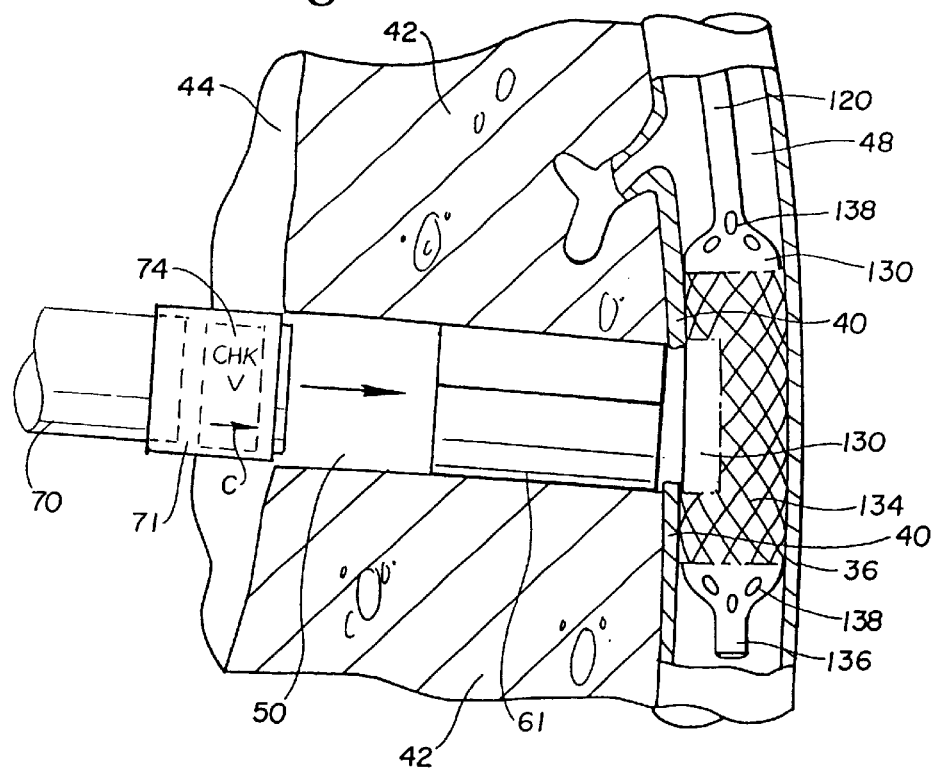
FIG. 17A is a cross-sectioned view of the left ventricle and a partial cutaway view of the coronary artery, with the device shown in FIGS. 15A and 15B seated within the formed channel, illustrating the introduction of a third intraventricular catheter into the formed channel.
Figure 17B:
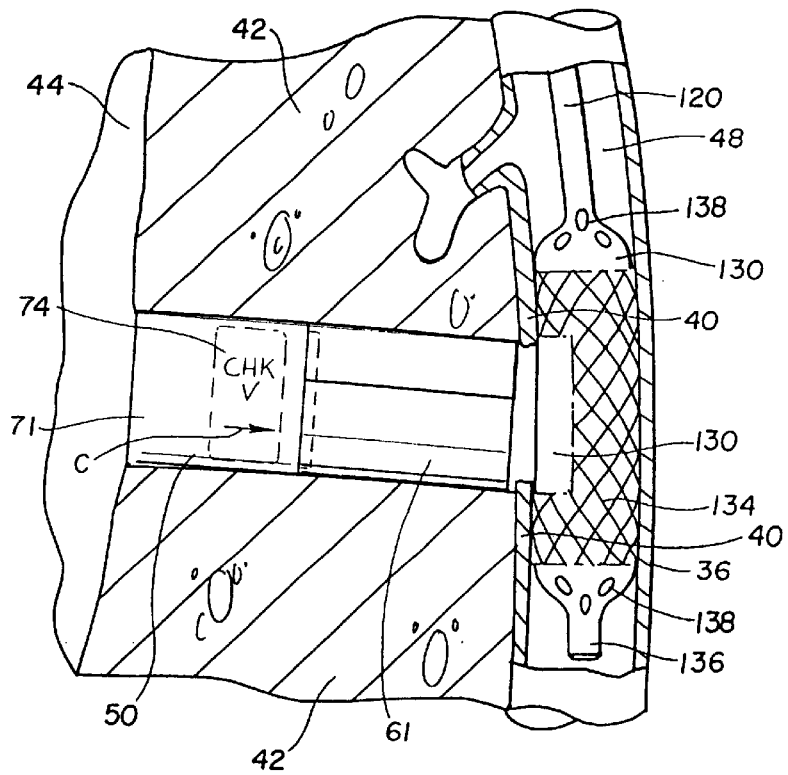
FIG. 17B is a cross-sectioned view of the left ventricle and a partial cutaway view of the coronary artery, with the device shown in FIGS. 15A and 15B seated within the formed channel, illustrating a tongue and groove interlocking of the bi-directional flow regulator equipped device to the device seated within the formed channel.

This third intraventricular catheter 70 is equipped with a hollow tube 71 on its distal tip which can interlock to the device 61 previously placed within the formed channel 50, as shown in FIGS. 17A and 17B.

Fifteenth, the hollow tube 71 is forwarded within the formed channel 50, and interlocked to the device 61. In one embodiment, the hollow tube 71 can partially insert into the device 61 previously seated within the formed channel 50.

The hollow tube 71 can, but may not necessarily, be equipped with a bi-directional flow regulator 74 to provide full blood flow in the direction of arrow C with reduced (but not blocked) blood flow opposite the direction of arrow C. An array of such hollow tubes 71 of various dimensions can be available to the surgeon at the operative procedure.

Sixteenth, the balloon 130 on the end of the intracoronary catheter 120 is deflated.

Seventeenth, angiographic dye can be introduced into a chamber of the heart through a port internal to the third intraventricular catheter 71. The introduction of angiographic dye can allow the blood flow to be visualized under fluoroscopy, digital subtraction angiography, or similar standard techniques. By such radiographic examination, blood flow directly from a chamber of a heart into a coronary artery can be ascertained. In cases where a bi-directional flow regulator 74 is utilized, the bi-directional flow from a chamber of a heart and into a coronary artery and the flow rates can be verified.

Eighteenth, the third intraventricular catheter 70 is withdrawn from the body through the innominate incision site 142.

Nineteenth, the intracoronary catheter 120 is withdrawn from the body through the femoral incision site 126.

Twentieth, the sites of the innominate incision 142 and femoral incision 126 are surgically re-approximated through standard closure techniques.

Twenty-first, anesthesia is reversed and the patient revived by standard techniques.

Changes and Modifications

Although the foregoing invention has been described in detail by way of illustration and example, for purposes of clarity of understanding, it will be obvious that changes and modifications may be practiced within the scope of the appended claims.

What is claimed is:

1. A method for revascularizing a coronary vessel from a heart chamber with a conduit through a heart wall, the conduit including a first end and a second end, the conduit defining an inner diameter transition that narrows as the transition extends from the first end toward the second end, the method comprising the steps of:

forming a blood flow pathway from the heart chamber through the heart wall and into the coronary vessel;

placing the conduit in the blood flow pathway with the first end of the conduit proximate to and in fluid communication with the heart chamber and the second end proximate to and in fluid communication with the coronary vessel, the first and second ends in fluid communication; and directing blood flow through the conduit from the first end to the second end.

2. The method of claim 1, wherein the blood flow pathway remains open during both systole and diastole.

3. The method of claim 1, wherein the inner diameter transition forms a venturi restriction within the conduit.

4. The method of claim 1, wherein the conduit is placed in the blood flow path so that the first end extends into the heart chamber beyond the heart wall.

5. The method of claim 1 wherein the inner diameter transition terminates at minimum inner diameter at an intermediate location between the first and second ends and a second inner diameter transition from the minimum inner diameter toward the second end is defined which enlarges as the transition extends from the minimum inner diameter toward the second end.

* * * * *